(12) United States Patent
Butler et al.

(10) Patent No.: US 8,906,648 B2
(45) Date of Patent: Dec. 9, 2014

(54) RECOMBINANT PRODUCTION OF VASCULAR ENDOTHELIAL GROWTH FACTOR

(71) Applicant: Genentech, Inc., South San Francisco, CA (US)

(72) Inventors: Michelle D. Butler, South San Francisco, CA (US); Jeffrey L. Cleland, San Carlos, CA (US); David W. Kahn, North Potomac, MD (US); Shelly Pizarro, South San Francisco, CA (US); Charles H. Schmelzer, Burlingame, CA (US); Marjorie E. Winkler, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/850,641

(22) Filed: Mar. 26, 2013

(65) Prior Publication Data

US 2013/0217867 A1   Aug. 22, 2013

Related U.S. Application Data

(63) Continuation of application No. 12/817,382, filed on Jun. 17, 2010, now abandoned, which is a continuation of application No. 11/613,012, filed on Dec. 19, 2006, now abandoned.

(60) Provisional application No. 60/807,432, filed on Jul. 14, 2006, provisional application No. 60/753,615, filed on Dec. 22, 2005.

(51) Int. Cl.
| | | |
|---|---|---|
| *C12P 21/06* | (2006.01) | |
| *A61K 38/18* | (2006.01) | |
| *C07K 14/00* | (2006.01) | |
| *C07K 1/14* | (2006.01) | |
| *C07K 14/47* | (2006.01) | |
| *C07K 14/52* | (2006.01) | |

(52) U.S. Cl.
CPC . *C07K 1/14* (2013.01); *C07K 14/47* (2013.01); *C07K 14/52* (2013.01)
USPC ............ 435/69.1; 424/124; 530/417; 514/8.1

(58) Field of Classification Search
None
See application file for complete search history.

(56) References Cited

U.S. PATENT DOCUMENTS

| | | |
|---|---|---|
| 4,169,950 A | 10/1979 | Ferguson |
| 4,511,502 A | 4/1985 | Builder et al. |
| 4,511,503 A | 4/1985 | Olson et al. |
| 4,512,922 A | 4/1985 | Jones et al. |
| 4,565,785 A | 1/1986 | Gilbert et al. |
| 4,673,641 A | 6/1987 | George et al. |
| 4,710,473 A | 12/1987 | Morris |
| 4,795,706 A | 1/1989 | Hsiung et al. |
| 5,077,392 A | 12/1991 | Rudolph et al. |
| 5,332,671 A | 7/1994 | Ferrara et al. |
| 5,410,026 A | 4/1995 | Chang et al. |
| 5,593,865 A | 1/1997 | Rudolph et al. |
| 5,700,665 A | 12/1997 | Legoux et al. |
| 5,856,142 A | 1/1999 | Legoux et al. |
| 6,632,425 B1 | 10/2003 | Li et al. |
| 6,783,953 B1 | 8/2004 | Gordon et al. |
| 7,611,711 B2 | 11/2009 | Alitalo et al. |
| 2003/0120042 A1 | 6/2003 | Yamada et al. |
| 2005/0119165 A1 | 6/2005 | Jue et al. |
| 2006/0199948 A1 | 9/2006 | Ejima et al. |

FOREIGN PATENT DOCUMENTS

| | | |
|---|---|---|
| EP | 0484401 B1 | 9/1996 |
| EP | 1124941 B1 | 9/2003 |
| EP | 1 449 848 A1 | 8/2004 |
| EP | 1500661 A1 | 1/2005 |
| EP | 1973942 | 10/2008 |
| JP | S61195698 A | 8/1986 |
| JP | 07039388 | 2/1995 |
| JP | H09501693 A | 2/1997 |
| JP | H11130798 A | 5/1999 |
| JP | 2004-505601 A | 2/2004 |
| WO | 95/07097 | 3/1995 |
| WO | 95/24473 | 9/1995 |
| WO | 9602562 A1 | 2/1996 |
| WO | 98/16551 | 4/1998 |
| WO | WO-99/42486 A1 | 8/1999 |
| WO | WO-99/50302 | 10/1999 |
| WO | 01/60861 A1 | 8/2001 |
| WO | WO-01/55174 A2 | 8/2001 |
| WO | 01/87925 A2 | 11/2001 |
| WO | 02/068455 A2 | 9/2002 |
| WO | 2004/092393 A1 | 10/2004 |
| WO | WO-2005/061712 A1 | 7/2005 |
| WO | WO-2005/097827 A1 | 10/2005 |
| WO | WO-2006/001023 A2 | 1/2006 |
| WO | WO-2006/053568 A1 | 5/2006 |

OTHER PUBLICATIONS

Anspach et al., "Purification of recombinant human basic fibroblast growth factor: stability of selective sorbents under cleaning in place conditions" J Chromatogr A. 711:129-139 (1995).

Arakawa et al., "Biotechnology applications of amino acids in proteins purification and formulations [Epub ahead of print]" Amino Acids (19 pages) (Mar. 16, 2007).

(Continued)

*Primary Examiner* — Elly-Gerald Stoica

(74) *Attorney, Agent, or Firm* — Clark & Elbing LLP; Karen L. Elbing

(57) ABSTRACT

A process for recovering and purifying refolded heparin binding proteins produced in heterologous host cells includes the step of incubation of the solubilized protein with a polyanionic species such as dextran sulfate.

16 Claims, 12 Drawing Sheets

(56) References Cited

OTHER PUBLICATIONS

Arakawa et al., "Suppression of protein interactions by arginine: a proposed mechanism of the arginine effects" Biophys Chem. 127:1-8 (2007).
Baneyx, "Recomninant protein expression in *Escherichia coli*" Curr Opin Biotechnol. 10:411-421 (1999).
Barzu et al., "Heparin-Derived Oligosaccharides: Affinity for Acidic Fibroblast Growth Factor and Effect on Its Growth-Promoting Activity for Human Endothelial Cells" J. Cell Phys. 140:538-548 (1989).
Bolivar et al., "Construction and Characterization of New Cloning Vehicles. II. A Multipurpose Cloning System" Gene 2:95-113 (1977).
Brandner et al., "Investigating the effect of VEGF glycosylation on glycosaminoglycan binding and protein unfolding" Biochemical and Biophysical Research Communications 340:836-839 (2006).
Brems and Stellwagon, "Manipulation of the observed kinetic phases in the refolding of denatured ferricytochromes c" J Biol Chem. 258(6):3655-3660 (Mar. 25, 1983).
Brinkmann et al., "Independent domain folding of *Pseudomonas* extoxin and single-chain immunotoxins: influence of interdomain connections" Proc Natl Acad Sci U S A. 89(7):3075-3079 (Apr. 1, 1992).
Buchner et al., "Renaturation, purification and characterization of recombinant Fab-fragments produced in *Exchericia coli*" Bio/Technology 9:157-162 (1991).
Burgess and Maciag, "The Heparin-Binding (Fibroblast) Growth Factor Family of Proteins" Annu. Rev. Biochem. 58:575-606 (1989).
Cao et al., "Heterodimer of placenta growth factor/vascular endothelial growth factor. Endothelial activity, tumor cell expression, and high affinity binding to Flk-1/KDR" Journal of Biological Chemistry 271(6):3154-3162 (Feb. 9, 1996).
Carrio and Villaverde, "Role of molecular chaperone in inclusion body formation" FEBS Letters 537:215-221 (2003).
Claffey ey al., "Structural requirements for dimerization, glycosylation, secretion, and biological function of VPF/VEGF" Biochimica et Biophysica Acta 1246:1-9 (1995).
Clark, "Refolding of recombinant proteins" Curr Opin Biotechnol. 9:157-163 (1998).
Cleland and Wang, "Refolding and aggregation of bovine carbonic anhydrase B: quasi-elastic light scattering analysis" Biochemistry 29:11072-11078 (1990).
Office Action issued on Nov. 12, 2010, in related Chinese Patent Application No. 200680052416.1,:8.
Creighton, "Folding of Proteins Adsorbed Reversibly to Ion-Exchanged Resins" Protein Structure, Folding, and Design, Alan R. Liss, Inc. pp. 249-257 (1986).
Dabora et al., "Effect of polyanions on the refolding of human acidic fibroblast growth factor" J Biol Chem. 266(35):23637-23640. (Dec. 15, 1991).
Estape and Rinas, "Optimized procedures for purification and solubilization of basic fibroblast growth factor inclusion bodies" Biotech. Tech. 10(7):481-484 (Jul. 1996).
Ferrara et al., "Purification and Cloning of Vascular Endothelial Growth Factor Secreted by Pituitary Folliculostellate Cells" Methods in Enzymology 198:391-405 (1991).
Ferrara et al., "The vascular endothelial growth family of polypeptides" J. Cell. Biochem. 47:211-218 (1991).
Ferrara et al., "Vascular endothelial growth factor: basic science and clinical progress" Endocr Rev. 25(4):581-611 (Aug. 2004).
Fischer et al., "Isolation, renaturation, and formation of disulfide bonds of eukaryotic proteins expressed in *Escherichia coli* as inclusion bodies" Biotechnology and Bioengineering 41:3-13 (1993).
Gengrinovitch et al., "Glypican-1 Is a VEGF$_{165}$ Binding Proteoglycan That Acts as an Extracellular Chaperone for VEGF$_{165}$" Journal of Biological Chemistry 274(16):10816-10822 (Apr. 16, 1999).
Gualandris et al., "Interaction of high-molecular-weight basic fibroblast growth factor with endothelium: biological activity and intracellular fate of human recombinant $M_r$ 24,000 bFGF" J Cell Physiol. 161:149-159 (1994).

Guo J. et al. et al., "The Expression of Recombinant Proteins in the Inclusion Body of *E coli* and Its Renaturation (Original and English Translation)" Scientific Technologic Information Pasturage Veterinarian 8:66-68 (2005).
Hagen et al., "Protein refolding in reversed micelles: Interactions of the protein with micelle components" Biotechnology and Bioengineering 35:966-975 (1990).
Heiring et al., "Folding screening assayed by proteolysis: application to various cystine deletion mutants of vascular endothelial growth factor" Protein Engineering 14(3):183-188 (2001).
Houck et al. et al., "The Vascular Endothelial Growth Factor Family: Identification of a Fourth Molecular Species and Characterization of Alternative Splicing of RNA" MOL Endocrinol 5(12):1806-14 (1991).
Ishibashi et al., "Is arginine a protein-denaturant?" Protein Expr Purif. 42:1-6 (2005).
Ishihara et al., "Preparation of Affinity-fractionated, Heparin-derived Oligosaccharides and Their Effects on Selected Biological Activities Mediated by Basic Fibroblast Growth Factor" Journal of Biological Chemistry 268:4675-4683 (1993).
Kajio et al., "Stabilization of basic fibroblast growth factor with dextran sulfate" FEBS Letters 306:243-246 (Jul. 1992).
Keck et al., "Disulfide Structure of the Heparin Binding Domain in Vascular Endothelial Growth Factor: Characterization of Post-translational Modifications in VEGF" Archives of Biochemistry & Biophysics 344(1):103-113 (Aug. 1, 1997).
Keyt et al., "Identification of Vascular Endothelial Growth Factor Determinants for Binding KDR and FLT-1 Receptors: Generation of Receptor-Selective VEGF Variants by Site-Directed Mutagenesis" Journal of Biological Chemistry 271(10):5638-5646 (Mar. 8, 1996).
Keyt et al., "The Carboxyl-terminal Domain (111-165) of Vascular Endothelial Growth Factor Is Critical for Its Mitogenic Potency" Journal of Biological Chemistry 271(13):7788-7795 (Mar. 29, 1996).
Kikuchi et al., "The nucleotide sequence of the promoter and the amino-terminal region of alkaline phosphatase structural gene (phoA) of *Escherichia coli*" Nucleic Acids Res 9(21):5671-5678 (1981).
Kipriyanov and Little, "Generation of Recombinant Antibodies" Mol. Biotech. 12:173-201 (1999).
Klagsbrun, M., "The Fibroblast Growth Factor Family: Structural and Biological Properties" Prog. Growth Factor Research 1:207-235 (1989).
Lee et al., "Characterization of the gene encoding heat-stable toxin II and preliminary molecular epidemiological studies of enterotoxigenic *Escherichia coli* heat-stable toxin II producers" :Infect Immun 42:264-268 (Oct. 1983).
Leung et al. et al., "Vascular Endothelial Growth Factor is a Secreted Angiogenic Mitogen" Science 246:1306-1309 (Dec. 8, 1989).
Lin and Traugh, "Renaturation of casein kinase II from recombinant subunits produced in *Escherichia coli*: purification and characterization of the reconstituted holoenzyme" Protein Expr Purif. 4:256-64 (1993).
Mach et al., "Partially Structured Self-Associating States of Acidic Fibroblast Growth Factor" Biochemistry 32:7703-7711 (1993).
McDonald et al., "(2375) Large Scale Production and Thorough Characterization of *E.coli* Expressed Basic Fibroblast Growth Factor-Saporin Mitotoxin" FASEB J. (bFGF) 9(3):A410 (1995).
Misawa and Kumagai, "Refolding of therapeutic proteins produced in *Escherichia coli* as inclusion bodies" Biopolymers 51:297-307 (1999).
Morris et al., "Monoclonal antibody studies of creatine kinase. Antibody-binding sites in the N-terminal region of creatine kinase and effects of antibody on enzyme refolding" Biochemical Journal 248:53-59 (1987).
Morris et al., "Protein folding/refolding analysis by mass spectrometry. Scrambling of disulphide bridges in insulin" Biochemical Journal 268:803-806 (1990).
Neu and Heppel, "The release of enzymes from *Escherichia coli* by osmotic shock and during the formation of spheroplasts" Journal of Biological Chemistry 240(9):3685-3692 (Sep. 1965).
Neu et al., "On the surface localization of enzymes in *E. coli*" Biochem Biophys Res Commun. 17(3):215-219 (1964).

(56) References Cited

OTHER PUBLICATIONS

Picken et al., "Nucleotide sequence of the gene of heat-stable enterotoxin II of *Escherichia coli*" Infect Immun 42(1):269-275 (Oct. 1983).

Potgens et al., "Covalent dimerization of vascular permeability factor/vascular growth factor is essential for its biological activity. Evidence from Cys to Ser mutations" J Biol Chem. 269(52):32879-32885 (Dec. 30, 1994).

Robinson and Stringer, "The splice variants of vascular endothelial growth factor (VEGF) and their receptors" J Cell Sci. 114(5):853-865 (Mar. 2001).

Rudolph and Life, "In vitro folding of inclusion body proteins" FASEB J. 10:49-56 (Jan. 1996).

Rudolph, "Renaturation Of Recombinant, Disulfide-Bonded Proteins From Inclusion Bodies" Modern Methods In Protein- and Nucleic Acid Research, Harald Tschesche, Berlin—New York:Walter de Gruyter pp. 149-171 (1990).

Scholtissek and Grosse et al., "A Cloning Cartridge of $\lambda t_o$ Terminator" Nucl Acids Res 15(7):3185 (1987).

Scrofani et al., "Towards a Structure-Function Relationship for Vascular Endothelial Growth Factor-B (VEGF-B)" J. Microbiol. Biotechnol. 11(4):543-551 (Aug. 2001).

Siemeister et al., "Expression of Biologically Active Isoforms of the Tumor Angiogenesis Factor VEGF in *Escherichia coli*" Biochem. & Biophys. Res. Comm. 222:249-255 (1996).

Simmons and Yansura, "Translational level is a critical factor for the secretion of heterologous proteins in *Escherichia coli*" Nat Biotechnol 14:629-634 (May 1996).

Skerra and Pluckthun, "Assembly of a functional immunoglobulin $F_v$ fragment in *Escherichia coli*" Science 240:1038-1041 (1988).

Taneja and Ahmad, "Increased thermal stability of proteins in the presence of amino acids" Biochemical Journal 303:147-153 (994).

Toren et al., "Determination of Interchain Crosslinkages in Insulin B-Chain Dimers by Fast Atom Bombardment Mass Spectrometry" Analytical Biochemistry 169:287-299 (1988).

Tsumoto et al., "Practical considerations in refolding proteins from inclusion bodies" Protein Expr Purif. 28:1-8 (2003).

Tsumoto et al., "Role of arginine in protein refolding, solubilization, and purification" Biotechnol. Prog. 20:1301-1308 (2004).

Villaverde and Carrió et al., "Protein aggregation in recombinant bacteria: biological role of inclusion bodies" Biotechnol Lett 25:1385-95 (, 2003).

Walter et al., "The in vivo bioactivity of vascular endothelial growth factor/vascular permeability factor is independent of N-linked glycosylation" Laboratory Investigation 74(2):546-556 (Feb. 1996).

Yang et al., "Substantially attenuated hemodynamic responses to *Escherichia coli*-derived vascular endothelial growth factor given by intravenous infusion compared with bolus injection" J. Pharm. Exp. Ther. 284(1):103-110 (1998).

Yanofsky et al., "The Complete Nucleotide Sequence of the Tryptophan Operon of *Escherichia coli*" Nucleic Acids Research 9(24):6647-6668 (Nov. 1981).

SEQUENCE LISTING

<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

```
Ala Pro Met Ala Glu Gly Gly Gly Gln Asn His His Glu Val Val
 1               5                  10                  15

Lys Phe Met Asp Val Tyr Gln Arg Ser Tyr Cys His Pro Ile Glu
                20                  25                  30

Thr Leu Val Asp Ile Phe Gln Glu Tyr Pro Asp Glu Ile Glu Tyr
                35                  40                  45

Ile Phe Lys Pro Ser Cys Val Pro Leu Met Arg Cys Gly Gly Cys
                50                  55                  60

Cys Asn Asp Glu Gly Leu Glu Cys Val Pro Thr Glu Glu Ser Asn
                65                  70                  75

Ile Thr Met Gln Ile Met Arg Ile Lys Pro His Gln Gly Gln His
                80                  85                  90

Ile Gly Glu Met Ser Phe Leu Gln His Asn Lys Cys Glu Cys Arg
                95                 100                 105

Pro Lys Lys Asp Arg Ala Arg Gln Glu Asn Pro Cys Gly Pro Cys
               110                 115                 120

Ser Glu Arg Arg Lys His Leu Phe Val Gln Asp Pro Gln Thr Cys
               125                 130                 135

Lys Cys Ser Cys Lys Asn Thr Asp Ser Arg Cys Lys Ala Arg Gln
               140                 145                 150

Leu Glu Leu Asn Glu Arg Thr Cys Arg Cys Asp Lys Pro Arg Arg
               155                 160                 165
```

RECOMBINANT PRODUCTION OF VASCULAR ENDOTHELIAL GROWTH FACTOR

RELATED APPLICATION

This application is a continuation of U.S. Ser. No. 12/817,382, filed on Jun. 17, 2010, which is a continuation of U.S. Ser. No. 11/613,012, filed on Dec. 19, 2006 which claims priority to and the benefit of U.S. Provisional Application Ser. No. 60/753,615, filed Dec. 22, 2005, and U.S. Provisional Application Ser. No. 60/807,432, filed Jul. 14, 2006, the specifications of which are incorporated herein in their entirety.

SEQUENCE LISTING

This application contains a Sequence Listing which has been submitted via EFS Web and is hereby incorporated by reference in its entirety. Said ASCII copy, created on Mar. 21, 2013, is named P2389R1C2-SeqList.txt and is 1,928 bytes in size.

FIELD OF THE INVENTION

This invention relates to methods for obtaining heparin-binding proteins produced in cell culture. The invention includes methods for recovering and purifying refolded heparin binding proteins that have been produced in prokaryotic host cells and are present in these cells, typically in the periplasmic or intracellular space. The heparin binding proteins produced in prokaryotic host cells can also be found as soluble proteins or a mixture of soluble and insoluble proteins.

BACKGROUND

It is known that a large variety of naturally occurring, biologically active polypeptides bind heparin. Such heparin-binding polypeptides include cytokines, such as platelet factor 4 and IL-8 (Barber et al., (1972) *Biochim. Biophys. Acta*, 286:312-329; Handin et al., (1976) *J. Biol. Chem.*, 251:4273-422; Loscalzo et al., (1985) *Arch. Biochem. Biophys.* 240: 446-455; Zucker et al., (1989) *Proc. Natl. Acad. Sci. USA*, 86:7571-7574; Talpas et al., (1991) *Biochim. Biophys. Acta*, 1078:208-218; Webb et al., (1993) *Proc. Natl. Acad. Sci. USA*, 90:7158-7162) heparin-binding growth factors (Burgess and Maciag, (1989) *Annu. Rev. Biochem.*, 58:576-606; Klagsbrun, (1989) *Prog. Growth Factor Res.*, 1:207-235), such as epidermal growth factor (EGF); platelet-derived growth factor (PDGF); basic fibroblast growth factor (bFGF); acidic fibroblast growth factor (aFGF); vascular endothelial growth factor (VEGF); and hepatocyte growth factor (HGF) (Liu et al., (1992) *Gastrointest. Liver Physiol.* 26:G642-G649); and selectins, such as L-selectin, E-selectin and P-selectin (Norgard-Sumnicht et al., (1993) *Science*, 261:480-483). See also, Munoz and Linhardt., (2004) *Arterioscler Thromb Vasc Biol.*, 24:1549-1557.

International Publication No. WO 95/07097 describes formulations of heparin binding proteins including heparin binding growth factors such as VEGF, with purified native heparin or other polyanionic compounds for therapeutic use. Heparin derived oligosaccharides and various other polyanionic compounds have been shown to stabilize the active conformation for heparin binding growth factors (Barzu et al., (1989) *J. Cell. Physiol.* 140:538-548; Dabora et al., (1991) *J. Biol. Chem.* 266:23627-23640) and heparin affinity chromatography has been employed in various purification schemes (see generally, International Publication No. WO 96/02562).

Many of the heparin binding proteins of mammalian origin have been produced by recombinant technology and are clinically relevant (Munoz and Linhardt, (2004) *Arterioscler Thromb Vasc Biol.*, 24:1549-1557; Favard et al. (1996) *Diabetes and Metabolism* 22(4):268-73; Matsuda et al., (1995) *J. Biochem.* 118(3):643-9; Roberts et al., (1995) *Brain Research* 699(1):51-61). For example, VEGF is a potent mitogen for vascular endothelial cells. It is also known as vascular permeability factor (VPF). See, Dvorak et al., (1995) *Am. J. Pathol.* 146:1029-39. VEGF play important roles in both vasculogenesis, the development of the embryonic vasculature, and angiogenesis, the process of forming new blood vessels from pre-existing ones. See, e.g., Ferrara, (2004) *Endocrine Reviews* 25(4):581-611; Risau et al., (1988) *Dev. Biol.*, 125:441-450; Zachary, (1998) *Intl. J. Biochem Cell Bio* 30:1169-1174; Neufeld et al., (1999) *FASEB J.* 13:9-22; Ferrara (1999) *J. Mol. Med.* 77:527-543; and, Ferrara and Davis-Smyth, (1997) *Endocri. Rev.* 18:4-25. Clinical applications for VEGF include those where the growth of new capillary beds is indicated as, for example, in promoting wound healing (see, for example, International Publication No. WO 91/02058; and, Ser. No. 11/455,017, entitled "Wound Healing" filed on Jun. 16, 2006), in promoting tissue growth and repair, e.g., liver (see, e.g., WO2003/0103581), bone (see, e.g., WO2003/094617), etc. See also, Ferrara, (2004) *Endocrine Reviews* 25(4):581-611.

Typically, therapeutically relevant recombinant proteins are produced in a variety of host organisms. Most proteins can be expressed in their native form in eukaryotic hosts such as CHO cells. Animal cell culture generally requires prolonged growing times to achieve maximum cell density and ultimately achieves lower cell density than prokaryotic cell cultures (Cleland, J. (1993) ACS Symposium Series 526, *Protein Folding: In Vivo and In Vitro*, American Chemical Society). Additionally, animal cell cultures often require expensive media containing growth components that may interfere with the recovery of the desired protein. Bacterial host expression systems provide a cost-effective alternative to the manufacturing scale production of recombinant proteins. Numerous U.S. patents on general bacterial expression of recombinant proteins exist, including U.S. Pat. Nos. 4,565,785; 4,673,641; 4,795,706; and 4,710,473. A major advantage of the production method is the ability to easily isolate the product from the cellular components by centrifugation or microfiltration. See, e.g., Kipriyanov and Little, (1999) *Molecular Biotechnology*, 12: 173-201; and, Skerra and Pluckthun, (1988) *Science*, 240: 1038-1040.

Recombinant heparin binding growth factors such as acidic fibroblast growth factor, basic fibroblast growth factor and vascular endothelial growth factor have been recovered and purified from a number of sources including bacteria (Salter D. H. et al., (1996) *Labor. Invest.* 74(2):546-556 (VEGF); Siemeister et al., (1996) *Biochem. Biophys. Res. Commun.* 222(2):249-55 (VEGF); Cao et al., (1996) *J. Biol. Chem.* 261(6):3154-62 (VEGF); Yang et al., (1994) *Gaojishu Tongxun*, 4:28-31 (VEGF); Anspach et al., (1995) *J. Chromatogr. A* 711(1):129-139 (aFGF and bFGF); Gaulandris (1994) *J. Cell. Physiol.* 161(1):149-59 (bFGF); Estape and Rinas (1996) *Biotech. Tech.* 10(7):481-484 (bFGF); McDonald et al., (1995) *FASEB J.* 9(3):A410 (bFGF)). However, bacterial expression systems such as *E. coli* lack the cellular machinery to facilitate proper refolding of the proteins and generally do not result in the secretion of large proteins into the culture media. Recombinant proteins expressed in bacterial host cells are often found as inclusion bodies consisting of dense masses of partially folded and misfolded reduced protein. In this form, the recombinant protein is generally inactive. For example, the predominant active form of VEGF is a homodimer of two 165-amino acid polypeptides (VEGF-165). In this structure, each subunit contains 7 pairs of intrachain disulfide bonds and two additional pairs which effect the covalent linkage of the two subunits (Ferrara et al., (1991) *J. Cell. Biochem.* 47:211-218). The native conformation includes a strongly basic domain which has been shown to readily bind heparin (Ferrara et al (1991) supra). Covalent dimerization of VEGF is needed for effective receptor binding and biological activity (Pötgens et al., (1994) *J. Biol. Chem.* 269:32879-32885; Claffey et al., (1995) *Biochim. et Biophys. Acta* 1246:1-9). The bacterial product potentially contains several misfolded and disulfide scrambled intermediates.

Additionally, refolding often produces misfolded and disulfide-linked dimers, trimers, and multimers. (Morris et al., (1990) *Biochem. J.*, 268:803-806; Toren et al., (1988) *Anal. Biochem.*, 169:287-299). This association phenomenon is very common during protein refolding, particularly at higher protein concentrations, and appears often to involve association through hydrophobic interaction of partially folded intermediates (Cleland and Wang, (1990) *Biochemistry*, 29:11072-11078).

Misfolding occurs either in the cell during fermentation or during the isolation procedure. Proteins recovered from periplasmic or intracellular space must be solubilized and the soluble protein refolded into the native state. In vitro methods for refolding the proteins into the correct, biologically active conformation are essential for obtaining functional proteins. Typical downstream processing of proteins recovered from inclusion bodies includes the dissolution of the inclusion body at high concentration of a denaturant such as urea followed by dilution of the denaturant to permit refolding to occur (see, U.S. Pat. Nos. 4,512,922; 4,511,502; and 4,511,503). See also, e.g., Rudolph and Lilie, (1996) *FASEB J.* 10:49-56; and, Fischer et al., (1993), *Biotechnology and Bioengineering*, 41:3-13. Such recovery methods are regarded as being universally applicable, with minor modifications, to the recovery of biologically active recombinant proteins from inclusion bodies. These methods have been applied to heparin binding protein such as VEGF (Siemeister et al. (1996) supra). These methods seek to eliminate random disulfide bonding prior to coaxing the recombinant protein into its biologically active conformation through its other stabilizing forces and may not eliminate improperly folded intermediates or provide homogenous populations of properly folded product.

Reversed micelles or ion exchange chromatography have been used to assist refolding of denatured proteins by enclosing a single protein within micelles or isolating them on a resin and then removing the denaturant (Hagen et al., (1990) *Biotechnol. Bioeng.* 35:966-975; Creighton (1985) in *Protein Structure Folding and Design* (Oxender, D. L. Ed.) pp. 249-251, New York: Alan R. Liss, Inc.). These methods have been useful in preventing protein aggregation and facilitating proper refolding. To alter the rate or extent of refolding, conformation-specific refolding has been performed with ligands and antibodies to the native structure of the protein (Cleland and Wang, (1993), in *Biotechnology*, (Rehm H.-J., and Reed G. Eds.) pp 528-555, New York, VCH). For example, creatine kinase was refolded in the presence of antibodies to the native structure (Morris et al., (1987) *Biochem. J.* 248:53-57). In addition to antibodies, ligands and cofactors have been used to enhance refolding. These molecules would be more likely to interact with the folding protein after formation of the native protein. Therefore, the folding equilibrium could be "driven" to the native state. For example, the rate of refolding of ferricytochrome c was enhanced by the extrinsic ligand for the axial position of the heme iron (Brems and Stellwagon, (1983) *J. Biol. Chem.* 258:3655-3661). Chaperone proteins have also been used to assist with protein folding. See, e.g., Baneyx, (1999) *Current Opinion in Biotechnology*, 10:411-421.

There is a need for new and more effective methods of folding and/or recovering heparin binding proteins from a host cell culture, e.g., for the efficient and economical production of heparin binding proteins in bacterial cell culture that provides for elimination or reduction of biologically inactive intermediates and improved recovery of a highly purified biologically active properly refolded protein and that is generally applicable to manufacturing scale production of the proteins. The invention addresses these and other needs, as will be apparent upon review of the following disclosure.

SUMMARY OF THE INVENTION

The invention provides a method for recovering and purifying refolded heparin binding proteins from cell culture. In particular the invention provides a method of recovering a heparin binding protein from prokaryotic host cells, e.g., bacterial cells. For example, a method comprises the steps of (a) isolating insoluble heparin binding protein from the periplasmic or intracellular space of said bacterial cells; (b) solubilizing said isolated insoluble heparin binding protein in a first buffered solution comprising a chaotropic agent and a reducing agent, and c) incubating said solubilized heparin binding protein in a second buffered solution comprising a chaotropic agent and a sulfated polyanionic agent for such a time and under such conditions that refolding of the heparin binding protein occurs; and (d) recovering said refolded heparin binding protein, wherein there is a 2 to 10 fold increase in protein concentration recovered by incubating with a sulfated polyanionic agent compared to a control. In one embodiment, the second buffered solution further comprises arginine. In one embodiment, the second buffered solution further comprises cysteine or a mild reducing agent.

In one embodiment of the invention, there is a, e.g., 2-8 fold increase in protein concentration of recovered biologically active refolded protein, or 2-5 fold increase in protein concentration of recovered biologically active refolded protein, or 3-5 fold increase in protein concentration of recovered biologically active refolded protein, or a 2-3 fold increase in protein concentration of recovered biologically active refolded protein. In another embodiment of the invention, there is a, e.g., greater than a 2.0 fold, a 2.5 fold, a 2.8 fold, a 3.0 fold, a 5-fold, a 6 fold, a 7.0 fold, an 8 fold, a 9 fold, etc., increase in protein concentration recovered of biologically active refolded protein. In one embodiment of the invention, there is a 3 to 5-fold increase in protein concentration of biologically active refolded VEGF.

The processes of the invention are broadly applicable to heparin binding proteins and especially to heparin binding growth factors and in particular, vascular endothelial growth factor (VEGF). In certain embodiments of the invention, the sulfated polyanionic agent is between about 3,000 and 10,000 daltons. In one embodiment, the sulfated polyanionic agent utilized in the production processes is a dextran sulfate, sodium sulfate or heparin sulfate. In one aspect, the dextran sulfate is between 3,000 daltons and 10,000 daltons.

The invention additionally provides processes and methods for purification of heparin binding proteins either alone or in connection with the recovery of the heparin binding protein as described herein. In a particular embodiment, purification methods include contacting said refolded heparin binding protein with a hydroxyapatite chromatographic support; a first hydrophobic interaction chromatographic support, a cationic chromatographic support and a second hydrophobic interaction chromatographic support and selectively eluting the heparin binding protein from each support. In another embodiment, a purification method comprises contacting said refolded heparin binding protein with a cation exchange support; a first hydrophobic interaction chromatographic support, and an ion exchange or mixed-media chromatographic support and selectively eluting the heparin binding protein from each support. It is contemplated that the steps for recovery steps can be performed in any order, e.g., sequentially or altering the order of the chromatographic supports. In certain embodiments of the invention, methods are provided for recovering and purifying refolded heparin binding proteins from manufacturing or industrial scale cell culture.

DETAILED DESCRIPTION

Definitions

"Heparin" (also referred to as heparinic acid) is a heterogenous group of highly sulfated, straight-chain anionic mucopolysaccharides, called glycosaminoglycans. Although others may be present, the main sugars in heparin are: α-L-iduronic acid 2-sulfate, 2-deoxy-2-sulfamino-α-glucose 6-sulfate, β-D-glucuronic acid, 2-acetamido-2-deoxy-α-D-glucose, and L-iduronic acid. These and optionally other sugars are joined by glycosidic linkages, forming polymers of varying sizes. Due to the presence of its covalently linked sulfate and carboxylic acid groups, heparin is strongly acidic. The molecular weight of heparin varies from about 3,000 to about 20,000 daltons depending on the source and the method of determination.

Native heparin is a constituent of various tissues, especially liver and lung, and mast cells in several mammalian species. Heparin and heparin salts (heparin sodium) are commercially available and are primarily used as anticoagulants in various clinical situations.

"Dextran sulfate" is a sulfate of dextran whose principal structure is a polymer of D-glucose. Glucose and optionally other sugars are joined by α-D(1-6) glycosidic linkages, forming polymers of varying sizes. Due to the presence of covalently linked sulfate, dextran sulfate is strongly acidic. The sulfur content is generally not less than 10%, and typically about 15%-20% with up to 3 sulfate groups per glucose molecule. The average molecular weight of dextran sulfate is from about 1,000 to about 40,000,000 daltons. Examples of dextran sulfate employable in the invention include the sulfate of the dextrans produced from microorganisms such as *Leuconostoc mesenteroides* and *L. dextranicum*.

"Polyanionic agent" as used within the scope of the invention is meant to describe commercially available purified native heparin preparations and compounds which are capable of binding to heparin binding proteins including other "polyanionic agents" such as sodium sulfate, heparin sulfate, heparan sulfate, pentosan(poly)sulfate, dextran, dextran sulfate, hyaluronic acid, chondroitin, chondroitin sulfate, dermatan sulfate, and keratan sulfate. Particularly useful within the context of the invention is a "sulfated polyanionic agent," such as for example, a sulfate derivative of a polysaccharide, such as heparin sulfate, dextran sulfate, the sulfates of the cyclodextrin produced by microorganisms such as *Bacillus macerans* described in U.S. Pat. No. 5,314,872 as well as sulfates of other glucans such as β-1,3 glucan sulfates, the β-1,3 glucan being produced by microorgansims belonging to the genus *Alcaligenes* or *Agrobacterium*, and chondroitin sulfate as well as sulfated heparin fragments.

Figure 4:
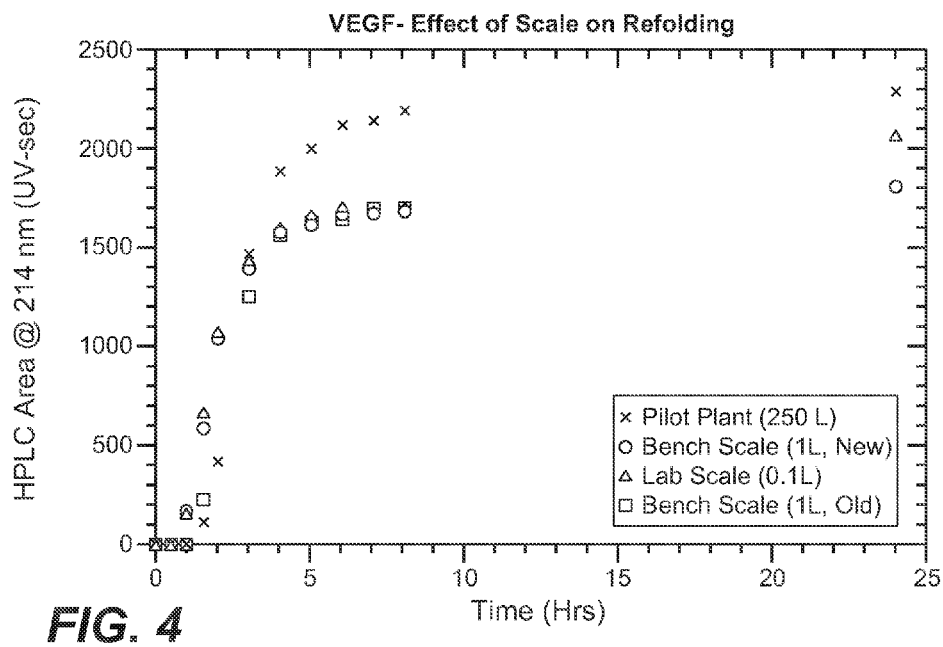
FIG. 4 illustrates the effect of scale on the refolding of VEGF.

The above mentioned agents are generally available and recognized by the skilled artisan. For example, sulfated heparin fragments may be obtained from a library of heparin-derived oligosaccharides that have been fractionated by gel-permeation chromatography. The preparation of affinity-fractionated, heparin-derived oligosaccharides was reported by Ishihara et al., (1993) *J. Biol. Chem.*, 268:4675-4683. These oligosaccharides were prepared from commercial porcine heparin following partial depolymerization with nitrous acid, reduction with sodium borohydride, and fractionation by gel permeation chromatography. The resulting pools of di-, tetra-, hexa-, octa-, and decasaccharides were sequentially applied to an affinity column of human recombinant bFGF covalently attached to SEPHAROSE™ 4B, and were further fractionated into subpools based on their elution from this column in response to gradients of sodium chloride. This resulted in five pools, designated Hexa-1 to Hexa-5, the structures and biological activities of which were further evaluated. The structure of Hexa-5C and its 500-MHz NMR spectrum are shown in FIG. 4 of Tyrell et al., (1993) *J. Biol. Chem.*, 268:4684-4689. This hexasaccharide has the structure [IdoA (2-OSO$_3$)α1-4GlcNSO$_3$(6-OSO$_3$)α1-4]$_2$IdoA(2-OSO$_3$)α1-4AMan$_R$(6-OSO$_3$). All heparin-derived oligosaccharides discussed above, as well as other heparin-like oligosaccharides are suitable for and can be used in accordance with the invention. In one embodiment of the invention, hexasaccharides and polysaccharides of heparin of higher unit size (e.g. hepta-, octa-, nona- and decasaccharides) are used. Furthermore, heparin-derived or heparin-like oligosaccharides with a large net negative charge, e.g. due to a high degree of sulfation, are used with advantage.

The term "heparin-binding protein" or "HPB" as used herein refers to a polypeptide capable of binding heparin (as hereinabove defined). The definition includes the mature, pre, pre-pro, and pro forms of native and recombinantly produced heparin-binding proteins. Typical examples of heparin-binding proteins are "heparin binding growth factors," including but not limited to epidermal growth factor (EGF), platelet derived growth factor (PDGF), basic fibroblast growth factor (bFGF), acidic fibroblast growth factor (aFGF), vascular endothelial growth factor (VEGF), hepatocyte growth factor (HGF) (also known as scatter factor, SF), and nerve growth factor (NGF), IL-8, etc.

Figure 11:
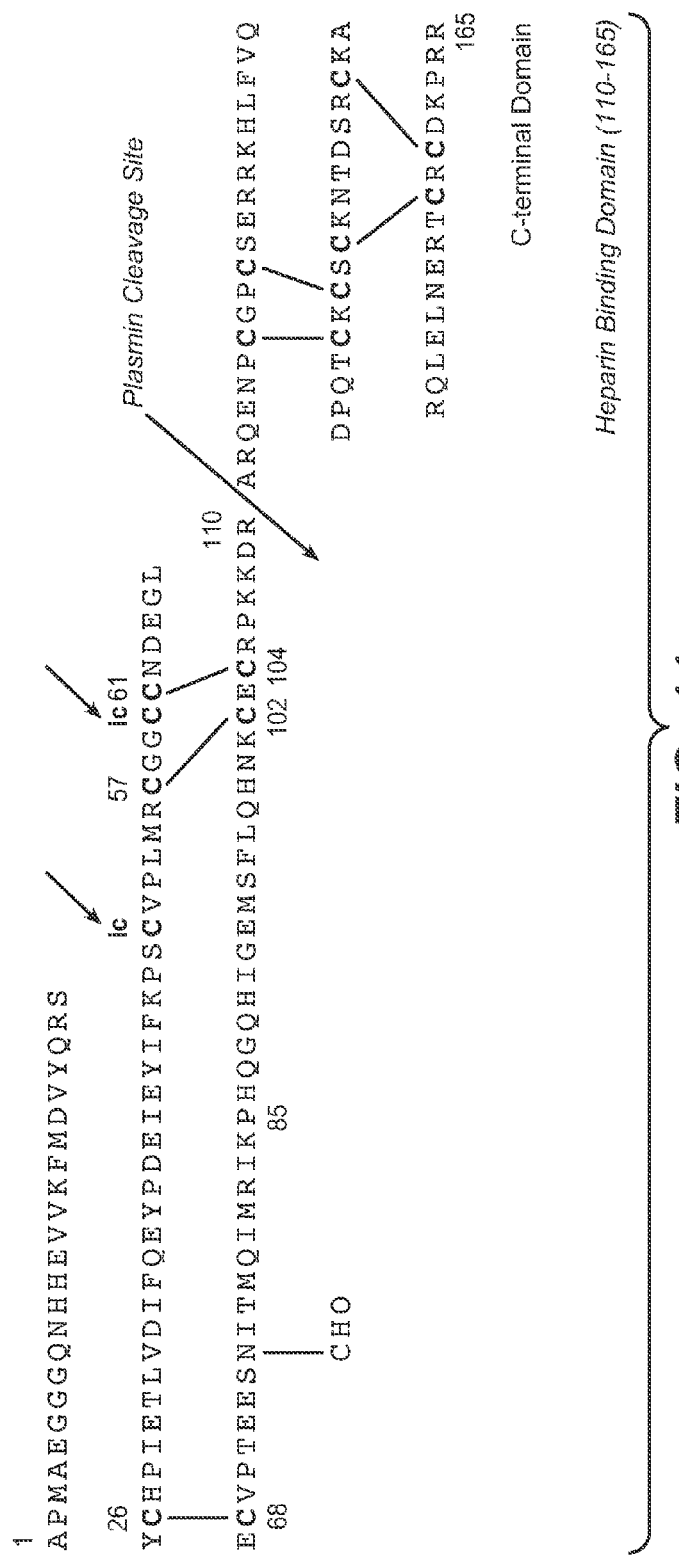
FIG. 11 illustrates the amino acid sequence of $VEGF_{165}$ with disulfide bonds indicated (SEQ ID NO.:1).

As used herein, "vascular endothelial growth factor", or "VEGF", refers to a mammalian growth factor derived originally from bovine pituitary follicular cells having the amino acid sequence disclosed in Castor, C. W., et al., (1991) *Methods in Enzymol.* 198:391-405, together with functional derivatives thereof having the qualitative biological activity of a corresponding native VEGF, including, but not limited to, the human VEGF amino acid sequence as reported in Houck et al., (1991) *Mol. Endocrin.* 5:1806-1814. See also, Leung et al. (1989) *Science*, 246:1306, and, Robinson & Stringer, (2001) *Journal of Cell Science*, 144(5):853-865, U.S. Pat. No. 5,332,671. The predominant form of VEGF is a 165 amino acid homodimer having sixteen cysteine residues that form 7 intramolecular disulfide bonds and two intermolecular disulfide bonds. Alternative splicing has been implicated in the formation of multiple human VEGF polypeptides consisting of 121, 145, 165, 189 and 206 amino acids, however the VEGF$_{121}$ variant lacks the heparin binding domain of the other variants and therefore does not fall within the definition of heparin binding protein set forth herein. All isoforms of VEGF share a common amino-terminal domain, but differ in the length of the carboxyl-terminal portion of the molecule. The preferred active form of VEGF, VEGF$_{165}$, has disulfide bonds between amino acid residues Cys26-Cys68; Cys57-Cys104; Cys6'-Cys102; Cys117-Cys135; Cys120-Cys137; Cys139-Cys; 158; Cys146-Cys160 in each monomer. See FIG. 11. See also, e.g., Keck et al., (1997) *Archives of Biochemistry and Biophysics* 344(1):103-113. The VEGF$_{165}$ molecule is composed of two domains: an amino-terminal receptor-binding domain (amino acids 1-110 disulfide linked homodimer) and a carboxyl-terminal heparin-binding domain (residues 111-165). See, e.g., Keyt et al., (1996) *J. Biol. Chem.*, 271(13):7788-7795. In certain embodiments of the invention, the VEGF$_{165}$ isolated and purified is not glycosylated at residue 75 (Asn). See, e.g., Yang et al., (1998) *Journal of Pharm. & Experimental Therapeutics*, 284:103-110. In certain embodiments of the invention, the VEGF$_{165}$ isolated and purified is substantially undeamidated at residue Asn10. In certain embodiments of the invention, the VEGF$_{165}$ isolated and purified is a mixture of deamidated (at residue Asn10) and undeamidated protein, typically with majority of the protein being undeamidated. Since VEGF$_{165}$ is a homodimer, deamination can occur on one or both polypeptide chains.

As used herein "properly folded" or "biologically active" VEGF or other HBP and the like refers to a molecule with a biologically active conformation. The skilled artisan will recognize that misfolded and disulfide scrambled intermediates may have biological activity. In such a case the properly folded or biologically active VEGF or HBP corresponds to the native folding pattern of the VEGF (described above) or other HBP. For example, properly folded VEGF has the above noted disulfide pairs, in addition to two intermolecular disulfide bonds in the dimeric molecule however other intermediates may be produced by bacterial cell culture (FIGS. 1 and 3A-3D). For properly folded VEGF the two intermolecular disulfide bonds occur between the same residues, Cys51 and Cys60, of each monomer. See, e.g., WO98/16551 patent. Biological activities of VEGF include, but are not limited to, e.g., promoting vascular permeability, promoting growth of vascular endothelial cells, binding to a VEGF receptor, binding and signaling through a VEGF receptor (see, e.g., Keyt et al., (1996) *Journal of Biological Chemistry*, 271(10):5638-5646), inducing angiogenesis, etc.

The terms "purified" or "pure HBP" and the like refer to a material free from substances which normally accompany it as found in its recombinant production and especially in prokaryotic or bacterial cell culture. Thus the terms refer to a recombinant HBP which is free of contaminating DNA, host cell proteins or other molecules associated with its in situ environment. The terms refer to a degree of purity that is at least about 75%, at least about 80%, at least about 85%, at least about 90%, at least about 95% or at least about 98% or more.

The terms "inclusion bodies" or "refractile bodies" refer to dense intracellular masses of aggregated polypeptide of interest, which constitute a significant portion of the total cell protein, including all cell components. In some cases, but not all cases, these aggregates of polypeptide may be recognized as bright spots visible within the enclosure of the cells under a phase-contrast microscope at magnifications down to 1,000 fold.

As used herein, the term "misfolded" protein refers to precipitated or aggregated polypeptides that are contained within refractile bodies. As used herein, "insoluble" or "misfolded" VEGF or other HBP refers to precipitated or aggregated VEGF that is contained within the periplasm or intracellular space of prokaryotic host cells, or is otherwise prokaryotic host cell associated, and assumes a biologically inactive conformation with mismatched or unformed disulfide bonds. The insoluble HBP is generally, but need not be, contained in refractile bodies, i.e., it may or may not be visible under a phase contrast microscope.

As used herein, "chaotropic agent" refers to a compound that, in a suitable concentration in aqueous solution, is capable of changing the spatial configuration or conformation of polypeptides through alterations at the surface thereof so as to render the polypeptide soluble in the aqueous medium. The alterations may occur by changing, e.g., the state of hydration, the solvent environment, or the solvent-surface interaction. The concentration of chaotropic agent will directly affect its strength and effectiveness. A strongly denaturing chaotropic solution contains a chaotropic agent in large concentrations which, in solution, will effectively unfold a polypeptide present in the solution effectively eliminating the proteins secondary structure. The unfolding will be relatively extensive, but reversible. A moderately denaturing chaotropic solution contains a chaotropic agent which, in sufficient concentrations in solution, permits partial folding of a polypeptide from whatever contorted conformation the polypeptide has assumed through intermediates soluble in the solution, into the spatial conformation in which it finds itself when operating in its active form under endogenous or homologous physiological conditions. Examples of chaotropic agents include guanidine hydrochloride, urea, and hydroxides such as sodium or potassium hydroxide. Chaotropic agents include a combination of these reagents, such as a mixture of a hydroxide with urea or guanidine hydrochloride.

As used herein, "reducing agent" refers to a compound that, in a suitable concentration in aqueous solution, maintains free sulfhydryl groups so that the intra- or intermolecular disulfide bonds are chemically disrupted. Representative examples of suitable reducing agents include dithiothreitol (DTT), dithioerythritol (DTE), beta-mercaptoethanol (BME), cysteine, cysteamine, thioglycolate, glutathione, Tris [2-carboxyethyl]phosphine (TCEP), and sodium borohydride.

As used herein, "buffered solution" refers to a solution which resists changes in pH by the action of its acid-base conjugate components.

The "bacteria" for purposes herein include eubacteria and archaebacteria. In certain embodiments of the invention, eubacteria, including gram-positive and gram-negative bacteria, are used in the methods and processes described herein. In one embodiment of the invention, gram-negative bacteria are used, e.g., Enterobacteriaceae. Examples of bacteria belonging to Enterobacteriaceae include *Escherichia, Enterobacter, Erwinia, Klebsiella, Proteus, Salmonella, Serratia*, and *Shigella*. Other types of suitable bacteria include *Azotobacter, Pseudomonas, Rhizobia, Vitreoscilla*, and *Paracoccus*. In one embodiment of the invention, *E. coli* is used. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting, and W3110 is one example. Mutant cells of any of the above-mentioned bacteria may also be employed. It is, of course, necessary to select the appropriate bacteria taking into consideration replicability of the replicon in the cells of a bacterium. For example, *E. coli, Serratia*, or *Salmonella* species can be suitably used as the host when well-known plasmids such as pBR322, pBR325, pACYC177, or pKN410 are used to supply the replicon. See further below regarding examples of suitable bacterial host cells.

As used herein, the expressions "cell," "cell line," "strain," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polypeptide" refers generally to peptides and proteins from any cell source having more than about ten amino acids. "Heterologous" polypeptides are those polypeptides foreign to the host cell being utilized, such as a human protein produced by *E. coli*. While the heterologous polypeptide may be prokaryotic or eukaryotic, preferably it is eukaryotic, more preferably mammalian, and most preferably human. In certain embodiments of the invention, it is a recombinantly produced, or recombinant polypeptide.

Heparin Binding Proteins
Isolating Heparin Binding Protein

Insoluble, misfolded heparin binding protein (HBP) is isolated from prokaryotic host cells expressing the protein by any of a number of art standard techniques. For example, the insoluble HBP is isolated in a suitable isolation buffer by exposing the cells to a buffer of suitable ionic strength to solubilize most host proteins, but in which the subject protein is substantially insoluble, or disrupting the cells so as to release the inclusion bodies or the protein form the periplasmic or intracellular space and make them available for recovery by, for example, centrifugation. This technique is well known and is described in, for example, U.S. Pat. No. 4,511, 503. Kleid et al., disclose purification of refractile bodies by homogenization followed by centrifugation (Kleid et al., (1984) in *Developments in Industrial Microbiology*, (Society for Industrial Microbiology, Arlington, Va.) 25:217-235). See also, e.g., Fischer et al., (1993) *Biotechnology and Bioengineering* 41:3-13.

U.S. Pat. No. 5,410,026 describes a typical method for recovering protein from inclusion bodies and is summarized as follows. The prokaryotic cells are suspended in a suitable buffer. Typically the buffer consists of a buffering agent suitable for buffering at between pH 5 to 9, or about 6 to 8 and a salt. Any suitable salt, including NaCl, is useful to maintain a sufficient ionic strength in the buffered solution. Typically an ionic strength of about 0.01 to 2 M, or 0.1 to 0.2 M is employed. The cells, while suspended in this buffer, are disrupted or lysed using techniques commonly employed such as, for example, mechanical methods, e.g., Homogenizer (Manton-Gaulin press, Microfluidizer, or Niro-Soavi), a French press, a bead mill, or a sonic oscillator, or by chemical or enzymatic methods.

Examples of chemical or enzymatic methods of cell disruption include spheroplasting, which entails the use of lysozyme to lyse the bacterial wall (H. Neu et al., (1964) *Biochem. Biophys. Res. Comm.*, 17:215), and osmotic shock, which involves treatment of viable cells with a solution of high tonicity and with a cold-water wash of low tonicity to release the polypeptides (H. Neu et al., 1965 *J. Biol. Chem.*, 240(9):3685-3692). Sonication is generally used for disruption of bacteria contained in analytical scale volumes of fermentation broth. At larger scales high pressure homogenization is typically used.

After the cells are disrupted, the suspension is typically centrifuged at low speed, generally around 500 to 15,000× g, e.g., in one embodiment of the invention about 12,000× g is used, in a standard centrifuge for a time sufficient to pellet substantially all of the insoluble protein. Such times can be simply determined and depend on the volume being centrifuged as well as the centrifuge design. Typically about 10 minutes to 0.5 hours is sufficient to pellet the insoluble protein. In one embodiment the suspension is centrifuged at 12,000×g for 10 minutes.

The resulting pellet contains substantially all of the insoluble protein fraction. If the cell disruption process is not complete, the pellet may also contain intact cells or broken cell fragments. Completeness of cell disruption can be assayed by resuspending the pellet in a small amount of the same buffer solution and examining the suspension with a phase contrast microscope. The presence of broken cell fragments or whole cells indicates that further sonication or other means of disruption is necessary to remove the fragments or cells and the associated non-refractile polypeptides. After such further disruption, if required, the suspension is again centrifuged and the pellet recovered, resuspended, and reexamined. The process is repeated until visual examination reveals the absence of broken cell fragments in the pelleted material or until further treatment fails to reduce the size of the resulting pellet.

The above process can be employed whether the insoluble protein is intracellular or in the periplasmic space. In one embodiment of the invention, the conditions given herein for isolating heparin binding protein are directed to inclusion bodies precipitated in the periplasmic space or intracellular space and relate particularly to VEGF. However, the processes and procedures are thought to be applicable to heparin binding proteins in general with minor modifications as noted throughout the following text. In certain embodiments of the invention, the processes and procedures are applicable to manufacturing or industrial scale production, refolding, and purification of the HBP.

Refolding Heparin Binding Proteins

The isolated insoluble, misfolded heparin binding protein is incubated in a first buffered solution containing an amount of a chaotropic agent and a reducing agent sufficient to substantially solubilize the heparin binding protein. This incubation takes place under conditions of concentration, incubation time, and incubation temperature that will allow solubilization of some or substantially all the heparin binding protein, and for unfolding to occur.

Measurement of the degree of solubilization in the buffered solution can be simply determined and is suitably carried out, for example, by turbidity determination, by analyzing fractionation between the supernatant and pellet after centrifugation, on reduced SDS-PAGE gels, by protein assay (e.g., the Bradford reagent protein assay (e.g., Pierce, Bio-Rad etc.)), or by HPLC.

The first buffered solution comprises a buffering agent suitable for maintaining the pH range of the buffer at least about 7.0, with the typical range being 7.5-10.5. In one embodiment, the pH for VEGF is pH 8.0. Examples of suitable buffers that will provide a pH within this latter range include TRIS-HCl (Tris[hydroxymethyl]aminomethane), HEPPS (N-[2-Hydroxyethyl]piperazine-N'-[3-propane-sulfonic acid]), HEPES (N-[2-Hydroxyethyl]piperazine-N'-[2-ethanesulfonic acid])), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), glycine, and sodium acetate. In one embodiment of the invention, the buffer herein is HEPPS at about pH 8.0. In a further embodiment, the buffers, e.g., such as HEPPS, are sulfated.

Chaotropic agents suitable for practicing this invention include, e.g., urea and salts of guanidine or thiocyanate, e.g., urea, guanidine hydrochloride, sodium thiocyanate, etc. The amount of chaotropic agent necessary to be present in the buffer is an amount sufficient to unfold the HBP in solution. In certain embodiments of the invention, a chaotrope is present at about between about 4 and 10 molar. In one embodiment of the invention, the chaotropic agent is urea at about 5-8 M, or at about 7 M. In another example, the chaotropic agent is guanidine hydrochloride at about 6-8 M.

Figure 9:
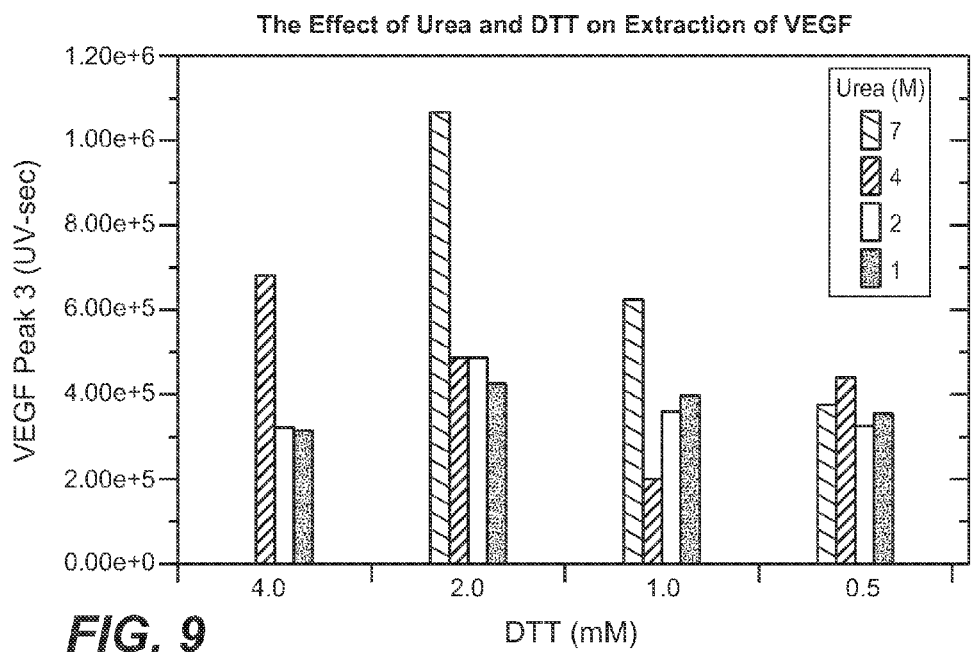
FIG. 9 illustrates an effect of urea and DTT on the extraction of VEGF from bacterial inclusion bodies.

Examples of suitable reducing agents include, but are not limited to, dithiothreitol (DTT), dithioerythritol (DTE), β-mercaptoethonol (BME), cysteine, DTE, etc. The amount of reducing agent to be present in the buffer will depend mainly on the type of reducing agent and chaotropic agent, the type and pH of the buffer employed, the amount of oxygen entrained in or introduced to the solution, and the concentration of the protein in the buffer. For example, with 0.5-1.5 mg/ml protein in a buffered solution at pH 7.0-10.0 containing 4-8 M urea, and reducing agent is, e.g., DTT with a concentration at about 1-15 mM, or BME with a concentration at about 0.2-2 mM, or cysteine with a concentration at about 2-10 mM. In one embodiment, the reducing agent is DTT at about 0.5 to about 4 mM, or 2-4 mM. FIG. 9 illustrates the effect of urea and DTT on the extraction of VEGF. Peak 3 VEGF refers to properly folded biologically active VEGF. In one embodiment, the reducing agent is DTT at about 10 mM. A single reducing agent or a combination of reducing agents can be used in a buffer herein.

The concentration of the protein in the buffered solution must be such that the protein will be substantially solubilized as determined by optical density. The exact amount to employ will depend on, e.g., the concentrations and types of other ingredients in the buffered solution, particularly the protein concentration, reducing agent, and the pH of the buffer. In one embodiment of the invention, the concentration of heparin binding protein is in the range of 0.5-5.5 mg per ml, or 1.5-5.0 mg/ml. The solubilization is typically carried out at about 0-45° C., or about 20-40° C., or about 23-37° C., or about 25-37° C., or about 25° C. for at least about one to 24 hours. In one embodiment, the solubilization is carried out for at least about two hours at room temperature. Typically, the temperature is not apparently affected by salt, reducing agent and chaotropic agent levels.

After the polypeptide is solubilized, it is placed or diluted into a second buffered solution containing the chaotropic agent and a sulfated polyanionic agent as described above however at a concentration of chaotropic agent which allows for refolding of the heparin binding protein.

The conditions of this second incubation of the soluble, misfolded protein will generally be such that some or substantial or complete refolding of the protein will take place. The exact conditions will depend on, for example, the pH of the buffer and the types and concentrations of sulfated polyanionic agents and of chaotropic and reducing agents, if any, present. The incubation temperature is generally about 0-40° C., or 10-40° C. and the incubation will generally be carried out for at least about 1 hour to effect refolding. In certain embodiments, the reaction is carried out, e.g., at about 15-37° C., or at 20-30° C., for at least about 6 hours, for at least about 10 hours, or between about 10 and 48 hours, or between about 15 and 20 hours, or between 6 and 20 hours, or between 12 and 24 hours.

The degree of refolding is suitably determined by radioimmuno assay (RIA) titer of the HPB or by high performance liquid chromatography (HPLC) analysis using e.g., a POROS HE2/M column (PerSeptive BioResearch Products) or other appropriate heparin affinity column. Increasing RIA titer or correctly folded HBP peak size directly correlates with increasing amounts of correctly folded, biologically active HPB present in the buffer. The incubation is carried out to maximize the ratio of correctly folded HPB to misfolded HPB recovered, as determined by RIA or HPLC.

In one embodiment, the quality and quantity of properly-folded VEGF is assessed using a heparin-binding assay. Samples containing the diluted heparin binding protein are loaded on a e.g., POROS HE2/M column (4.6×100 mm, PerSeptive BioResearch Products, Cambridge, Mass.) or other suitable heparin affinity column. For example, the heparin affinity column is equilibrated in 10 mM sodium phosphate, pH 7 containing 0.15 M sodium chloride. At a flow rate of 1 ml/min or 2 ml/min, the column is eluted using a linear gradient from 0.15-2 M sodium chloride in, 10 mM sodium phosphate, pH 7 over 10 minutes. The eluant is monitored at 280 nm. In one embodiment, the protein is recovered in a single peak corresponding to the biologically active properly refolded HBP. In one embodiment of the invention, an assay for determining properly refolded HBP is RPHPLC. Disulfide linkages can optionally be confirmed by peptide map. Circular dichroism can also be used in for determining 2 & 3D structure/folding.

The buffer for the second buffered solution can be any of those listed above for the first buffered solution, e.g., HEPPS pH. 8.0, e.g., at a concentration of about 50 mM for refolding VEGF. The polypeptide may be diluted with the refolding buffer, e.g., at least five fold, or at least about ten fold, about 20 fold, or about 40 fold. Alternatively, the polypeptide may be dialyzed against the refolding buffer.

Figure 10:
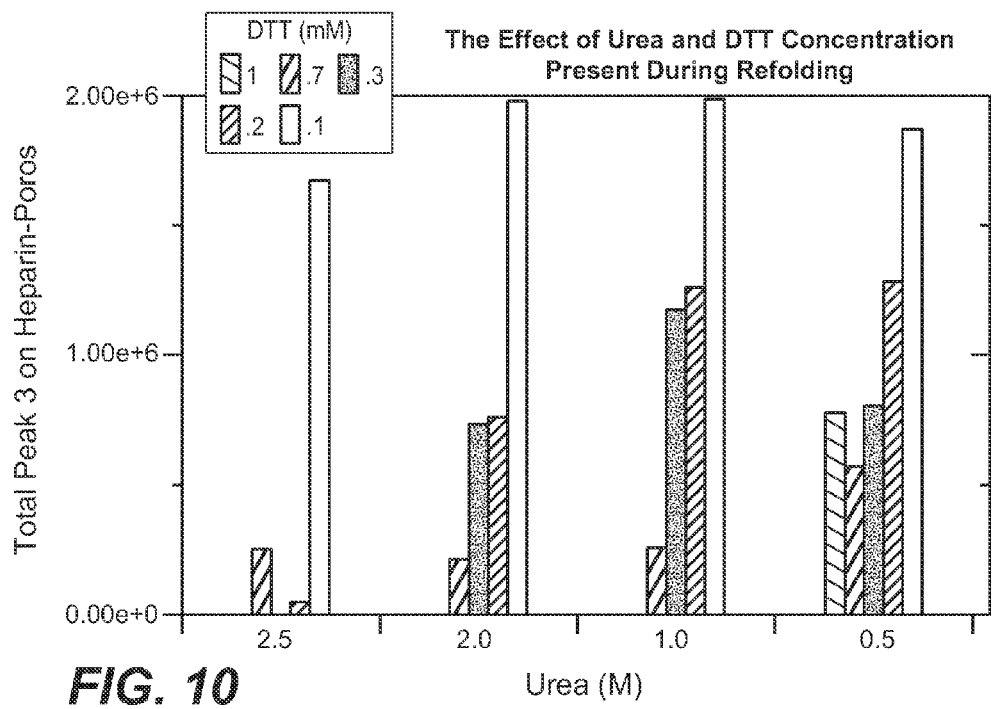
FIG. 10 illustrates an effect of urea and DTT concentration on the refolding of VEGF.

The second buffered solution contains a chaotropic agent at a concentration such that refolding of the HPB occurs. Generally a chaotrope is present at about between about 0.5 and 2 molar. In one embodiment of the invention, the chaotropic agent herein is urea at about 0.5-2 M, 0.5-2 M, or at about 1 M. In one embodiment, the chaotropic agent is urea at about 1.3 M concentration. In another embodiment of the invention, the chaotropic agent is guanidine hydrochloride at about 1 M. FIG. 10 illustrates the effect of urea and reducing agent DTT on the refolding of VEGF. Peak 3 VEGF refers to properly folded biologically active VEGF.

As noted, the solution optionally also contains a reducing agent. The reducing agent is suitably selected from those described above for the solubilizing step in the concentration range of about 0.5 to about 10 mM for cysteine, 0.1-1.0 mM for DTT, and/or less than about 0.2 mM for BME. In one embodiment of the invention, the reducing agent is DTT at about 0.5-2 mM. In one embodiment of the invention, the reducing agent is DTT at about 0.5 mM. Examples of suitable reducing agents include, but are not limited to, e.g., dithiothreitol (DTT), β-mercaptoethonol (BME), cysteine, DTE, etc. Whereas DTT and BME can be used in connection with the procedures provided herein for heparin binding proteins in general, a combination of cysteine at about 0.1 to about 10 mM and about 0.1 to about 1.0 mM DTT as described herein is an example for the recovery of VEGF.

The refolding step includes a sulfated polyanionic agent at a concentration sufficient to achieve complete refolding of the solubilized protein. Examples of suitable polyanionic agents are described herein above, e.g., a sulfate derivative of a polysaccharide as noted above with sulfated polyanionic agents such as heparin sulfate, dextran sulfate, heparin sulfate, and chrondroitin sulfate as well as sulfated heparin fragments. For heparin sulfates used in the context of the invention, the molecular weight are generally between about 3,000 and 10,000 daltons, or between about 3,000 and 6,000 dalton.

In one embodiment of the invention, dextran sulfate is employed in the context of the invention. The molecular weight of the sulfated polyanionic or other agent such as dextran sulfate employed in the invention depends upon the size of the particular heparin binding protein being recovered. Generally, dextran sulfate between about 3,000 and 10,000 daltons is employed. In one embodiment of the invention, dextran sulfate between about 5,000 daltons and 10,000 daltons is used, e.g., for the recovery of VEGF. In another embodiment, a dextran sulfate between about 5,000 and 8,000 daltons is used for recovery of the HBP. FIG. 3A-3D shows the recovery of VEGF with various concentrations of and molecular weights of dextran sulfate (FIGS. 3A-C) and heparin (FIG. 3D) as analyzed by heparin affinity chromatography. Peak 3 corresponds to properly folded VEGF.

The concentration of the polyanionic compound employed depends upon the protein being recovered and its concentration and conditions such as temperature and pH of the refolding buffer. Typical concentrations are between about 50 and 500 mM for sodium sulfate, between about 10 and 200 µg/ml for low molecular weight heparins such as 6,000 dalton heparin (Sigma Chemical Co.), between about 10 and 200 µg/ml for high molecular weight heparins such as porcine heparin I-A (Sigma Chemical Co.) and between about 10 and 400 µg/ml, or between about 10 and 200 µg/ml for dextran sulfates.

The refolding buffer can optionally contain additional agents such as any of a variety of non-ionic detergents such as TRITON™ X-100, NONIDET™ P-40, the TWEEN™ series and the BRIJ™ series. The non-ionic detergent is present at about between 0.01% and 1.0%. In one example, the concentrations for non ionic detergent are between about 0.025% and 0.05%, or about 0.05%.

Optionally, positively charged amino acids, e.g., arginine (e.g., L-arginine/HCl), lysine, etc., can be present in the refolding buffer. In certain embodiments of the invention, the concentration of arginine is e.g., about 0-1000 mM, or about 25 to 750 mM, or about 50-500 mM, or about 50-250 mM, or about 100 mM final concentration, etc. In certain embodiments of the invention, the protein is in a buffer solution at pH 7.0-9.0 containing, 0.5-3 M urea, 0-30 mg/L dextran sulfate, 0-0.2% Triton X-100, 2-15 mM cysteine, 0.1-1 mM DTT and 0-750 mM arginine, final concentration. In one embodiment, 50 mM HEPPS is used. In one embodiment, the final concentration of the refolding buffer solution is 1 M urea, 50 mM HEPPS, 15 mg/L dextran sulfate, 0.05% Triton X-100, 7.5 mM cysteine, 100 mM arginine, pH 8.0. In one embodiment, the final concentration of the refolding buffer solution is 1.3 M urea, 50 mM HEPPS, 15 mg/L dextran sulfate, 0.05% Triton X-100, 7.5 mM cysteine, 0.5 mM DTT, 100 mM arginine, pH 8.0.

Recovery and Purification of Heparin Binding Proteins

Although recovery and purification of the heparin binding protein from the culture media can employ various methods and known procedures for the separation of such proteins such as, for example, salt and solvent fractionation, adsorption with colloidal materials, gel filtration, ion exchange chromatography, affinity chromatography, immunoaffinity chromatography, electrophoresis and high performance liquid chromatography (HPLC), an example of a four step chromatographic procedure is described which comprises contacting said refolded heparin binding protein with a hydroxyapatite chromatographic support; a first hydrophobic interaction chromatographic support, a cationic chromatographic support and a second hydrophobic interaction chromatographic support and selectively eluting the heparin binding protein from each support. Alternatively, another chromatographic procedure is described which comprises contacting said refolded heparin binding protein with a cation exchange support; a hydrophobic interaction chromatographic support, and an ion exchange chromatographic support and selectively eluting the heparin binding protein from each support. It is contemplated that the steps of either procedure can be performed in any order. In one embodiment of the invention, the steps are performed sequentially.

A suitable first step in the further recovery and purification of the heparin binding protein characteristically provides for the concentration of the heparin binding protein and a reduction in sample volume. For example, the second incubation step described above, may result in a large increase in the volume of the recovered heparin binding protein and concomitant dilution of the protein in the refolding buffer. Suitable first chromatographic supports provide a reduction in volume of recovered heparin binding protein and may advantageously provide some purification of the protein from unwanted contaminating proteins. Suitable first chromatographic steps include chromatographic supports which can be eluted and loaded directly onto a first hydrophobic interaction chromatographic support. For example, chromatographic supports from which the heparin binding protein can be eluted in a high salt concentration suitable for loading a hydrophobic interaction chromatographic support are used.

Exemplary first chromatographic supports include, but are not limited to, hydroxyapatite chromatographic supports, e.g., CHT ceramic type I and type II(formally known as MacroPrep ceramic), Bio-Gel HT, Bio-Gel HTP, Biorad, Hercules, Calif., etc.; metal chelating chromatographic supports consisting of an inert resin of immobilized metal ions such as copper, nickel, etc.; as well as non-derivatized silica gels. In one embodiment of the invention, the first chromatographic supports for the purification and recovery of VEGF are hydroxyapatite chromatographic supports. In another embodiment of the invention, the first chromatographic supports for the purification and recovery of VEGF are cation exchange supports, e.g., described below in more detail.

Elution from the first chromatographic support is accomplished according to art standard practices. Suitable elution conditions and buffers will facilitate the loading of the eluted HPB directly onto the first hydrophobic interaction chromatographic support as described below.

Hydrophobic interaction chromatography is well known in the art and is predicated on the interaction of hydrophobic portions of the molecule interacting with hydrophobic ligands attached to "chromatographic supports." A hydrophobic ligand coupled to a matrix is variously referred to as an HIC chromatographic support, HIC gel, or HIC column and the like. It is further appreciated that the strength of the interaction between the protein and the HIC column is not only a function of the proportion of non-polar to polar surfaces on the protein but of the distribution of the non-polar surfaces as well.

A number of matrices may be employed in the preparation of HIC columns. The most extensively used is agarose, although silica and organic polymer resins may be used. Useful hydrophobic ligands include but are not limited to alkyl groups having from about 2 to about 10 carbon atoms, such as butyl, propyl, or octyl, or aryl groups such as phenyl. Conventional HIC supports for gels and columns may be obtained commercially from suppliers such as GE Healthcare, Uppsala, Sweden under the product names butyl-SEPHAROSE™, phenyl-SEPHAROSE™ CL-4B, octyl SEPHAROSE™ FF and phenyl SEPHAROSE™ FF and Tosoh Corporation, Tokyo, Japan under the product names TOYOPEARL™ butyl 650 M (Fractogel TSK Butyl-650) or TSK-GEL phenyl 5PW. In one embodiment, the purification and recovery of VEGF is a first HIC chromatographic support that is butyl-agarose and a second hydrophobic chromatographic support that is a phenyl agarose. In another embodiment, the first HIC chromatographic support is phenyl agarose.

Ligand density is an important parameter in that it influences not only the strength of the interaction of the protein but the capacity of the column as well. The ligand density of the commercially available phenyl or octyl phenyl gels is on the order of 5-40 μmmol/ml gel bed. Gel capacity is a function of the particular protein in question as well as pH, temperature and salt concentration but generally can be expected to fall in the range of 3-20 mg/ml gel.

The choice of particular gel can be determined by the skilled artisan. In general the strength of the interaction of the protein and the HIC ligand increases with the chain length of the alkyl ligands but ligands having from about 4 to about 8 carbon atoms are suitable for most separations. A phenyl group has about the same hydrophobicity as a pentyl group, although the selectivity can be different owing to the possibility of pi-pi interaction with aromatic groups of the protein.

Adsorption of the protein to a HIC column is favored by high salt concentration, but the actual concentration can vary over a wide range depending of the nature of the protein and the particular HIC ligand chosen. In general salt concentration between about 1 and 4 M are useful.

Elution from an HIC support, whether stepwise or in the form of a gradient, can be accomplished in a variety of ways such as a) by changing the salt concentration, b) by changing the polarity of the solvent or c) by adding detergents. By decreasing salt concentrations adsorbed proteins are eluted in order of increasing hydrophobicity. Changes in polarity may be effected by additions of solvents such as ethylene glycol or isopropanol thereby decreasing the strength of the hydrophobic interactions. Detergents function as displacers of proteins and have been used primarily in connection with the purification of membrane proteins.

Various anionic constituents may be attached to matrices in order to form cationic supports for chromatography. Anionic constituents include carboxymethyl, sulfethyl groups, sulfopropyl groups, phosphate and sulfonate (S). Cellulosic ion exchange resins such as SE52 SE53, SE92, CM32, CM52, CM92, P11, DE23, DE32, DE52, EXPRESS ION™ S and EXPRESS ION™ C are available from Whatman LTD, Maidstone Kent U.K. SEPHADEX™ and SEPHAROSE™ based and cross linked ion exchangers are also known under the product names CM SEPHADEX™ C-25, CM SEPHADEX™ C-50 and SP SEPHADEX™ C-25 SP SEPHADEX™ C-50 and SP-SEPHAROSE™ High Performance, SP-SEPHAROSE™ Fast Flow, SP-SEPHAROSE XL, CM-SEPHAROSE™ Fast Flow, and CM-SEPHAROSE™, CL-6B, all available from GE Healthcare. Examples of ion exchangers for the practice of the invention include but are not limited to, e.g., ion exchangers under the product names MACROPREP™ such as for example MACROPREP™ S support, MACROPREP™ High S support and MACROPREP™ CM support from BioRad, Hercules, Calif.

Elution from cationic chromatographic supports is generally accomplished by increasing salt concentrations. Because the elution from ionic columns involves addition of salt and because, as mentioned, HIC is enhanced in salt concentration the introduction of HIC step following the ionic step or other salt step is optionally used. In one embodiment of the invention, a cationic exchange chromatographic step precede the HIC step.

Examples of methods for purifying VEGF is described herein below, e.g., see Example V and VI. After refolding, insoluble material in the pool is removed by depth filtration. The clarified pool is then loaded on to a ceramic hydroxyapatite (Bio Rad, Hercules, Calif.) equilibrated in 5-mM HEPPS/0.05% TRITON™ X100/pH 8. The non-binding protein is removed by washing with equilibration buffer and the VEGF eluted using an isocratic step of 50 mM HEPPS/0.05% TRITON™ X100/0.15 M sodium phosphate/pH 8. The pool of VEGF is loaded onto a column of Butyl SEPHAROSE™ Fast Flow (GE Healthcare, Uppsala, Sweden) equilibrated in 50 mM HEPPS/0.05% TRITON™ X100/0.15 M sodium phosphate/pH 8. The column is washed with equilibration buffer and the VEGF collected in the column effluent. The Butyl SEPHAROSE™ pool is loaded onto a column of Macro Prep High S (BioRad, Hercules, Calif.) that is equilibrated in 50 mM HEPES/pH 8. After washing the effluent absorbance at 280 nm to baseline, the column is washed with two column volumes of 50 mM HEPES/0.25 M sodium chloride/pH 8. The VEGF is eluted using a linear, 8-column-volume gradient from 0.25-0.75 M sodium chloride in 50 mM HEPES/pH 8. Fractions are collected and those which contained properly-folded VEGF, as determined by a heparin-binding assay, are pooled.

The Macro Prep High S pool is conditioned with an equal volume of 50 mM HEPES/0.8 M sodium citrate/pH 7.5. The conditioned pool is then loaded on to a column of Phenyl 5PW TSK (Tosoh Bioscience LLC, Montgomeryville, Pa.) that is equilibrated with 50 mM HEPES/0.4 M sodium citrate/pH 7.5. After washing non-binding protein through the column with equilibration buffer, the VEGF is eluted from the column using a 10-column-volume gradient from 0.4-0 M sodium citrate in 50 mM HEPES, pH 7.5. Fractions are assayed by SDS-polyacrylamide gel electrophoresis and those containing VEGF of sufficient purity pooled.

Expressing Heparin Binding Protein in Host Cells

In brief, expression vectors capable of autonomous replication and protein expression relative to the host prokaryotic cell genome are introduced into the host cell. Construction of appropriate expression vectors is well known in the art including the nucleotide sequences of the heparin binding proteins described herein. See, e.g., Sambrook et al., *Molecular Cloning, A Laboratory Manual*, Cold Spring Harbor Laboratory Press (Cold Spring Harbor, N.Y.) (2001); Ausubel et al., *Short Protocols in Molecular Biology*, Current Protocols John Wiley and Sons (New Jersey) (2002); and, Baneyx, (1999) *Current Opinion in Biotechnology*, 10:411-421. Appropriate prokaryotic cell, including bacteria, expression vectors are available commercially through, for example, the American Type Culture Collection (ATCC), Rockville, Md. Methods for the large scale growth of prokaryotic cells, and especially bacterial cell culture are well known in the art and these methods can be used in the context of the invention.

For example, prokaryotic host cells are transfected with expression or cloning vectors encoding the heparin binding protein of interest and cultured in conventional nutrient media modified as appropriate for inducing promoters, selecting transformants, or amplifying the genes encoding the desired sequences. The nucleic acid encoding the polypeptide of interest is suitably RNA, cDNA, or genomic DNA from any source, provided it encodes the polypeptide(s) of interest. Methods are well known for selecting the appropriate nucleic acid for expression of heterologous polypeptides (including variants thereof) in microbial hosts. Nucleic acid molecules encoding the polypeptide are prepared by a variety of methods known in the art. For example, a DNA encoding VEGF is isolated and sequenced, e.g., by using oligonucleotide probes that are capable of binding specifically to the gene encoding VEGF.

The heterologous nucleic acid (e.g., cDNA or genomic DNA) is suitably inserted into a replicable vector for expression in the microorganism under the control of a suitable promoter. Many vectors are available for this purpose, and selection of the appropriate vector will depend mainly on the size of the nucleic acid to be inserted into the vector and the particular host cell to be transformed with the vector. Each vector contains various components depending on the particular host cell with which it is compatible. Depending on the particular type of host, the vector components generally include, but are not limited to, one or more of the following: a signal sequence, an origin of replication, one or more marker genes, a promoter, and a transcription termination sequence.

In general, plasmid vectors containing replicon and control sequences that are derived from species compatible with the host cell are used in connection with microbial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., (1977) *Gene*, 2: 95). pBR322 contains genes for ampicillin and tetracycline resistance and thus provides easy means for identifying transformed cells. The pBR322 plasmid, or other bacterial plasmid or phage, also generally contains, or is modified to contain, promoters that can be used by the host for expression of the selectable marker genes.

(i) Signal Sequence

Polypeptides of the invention may be produced recombinantly not only directly, but also as a fusion polypeptide with a heterologous polypeptide, which is typically a signal sequence or other polypeptide having a specific cleavage site at the N-terminus of the mature protein or polypeptide. The heterologous signal sequence selected typically is one that is recognized and processed (i.e., cleaved by a signal peptidase) by the host cell. For prokaryotic host cells that do not recognize and process the native polypeptide signal sequence, the signal sequence is substituted by a prokaryotic signal sequence selected, for example, from the group of the alkaline phosphatase, penicillinase, 1 pp, or heat-stable enterotoxin II leaders.

(ii) Origin of Replication Component

Expression vectors contain a nucleic acid sequence that enables the vector to replicate in one or more selected host cells. Such sequences are well known for a variety of microbes. The origin of replication from the plasmid pBR322 is suitable for most Gram-negative bacteria such as *E. coli*.

(iii) Selection Gene Component

Expression vectors generally contain a selection gene, also termed a selectable marker. This gene encodes a protein necessary for the survival or growth of transformed host cells grown in a selective culture medium. Host cells not transformed with the vector containing the selection gene will not survive in the culture medium. This selectable marker is separate from the genetic markers as utilized and defined by this invention. Typical selection genes encode proteins that (a) confer resistance to antibiotics or other toxins, e.g., ampicillin, neomycin, methotrexate, or tetracycline, (b) complement auxotrophic deficiencies other than those caused by the presence of the genetic marker(s), or (c) supply critical nutrients not available from complex media, e.g., the gene encoding D-alanine racemase for Bacilli.

One example of a selection scheme utilizes a drug to arrest growth of a host cell. In this case, those cells that are successfully transformed with the nucleic acid of interest produce a polypeptide conferring drug resistance and thus survive the selection regimen. Examples of such dominant selection use the drugs neomycin (Southern et al., (1982) *J. Molec. Appl. Genet.*, 1: 327), mycophenolic acid (Mulligan et al., (1980) *Science* 209: 1422) or hygromycin (Sugden et al., (1985) *Mol. Cell. Biol.*, 5: 410-413). The three examples given above employ bacterial genes under eukaryotic control to convey resistance to the appropriate drug G418 or neomycin (geneticin), xgpt (mycophenolic acid), or hygromycin, respectively.

(iv) Promoter Component

The expression vector for producing the heparin binding protein of interest contains a suitable promoter that is recognized by the host organism and is operably linked to the nucleic acid encoding the polypeptide of interest. Promoters suitable for use with prokaryotic hosts include the beta-lactamase and lactose promoter systems (Chang et al., (1978) *Nature*, 275: 615; Goeddel et al., (1979) *Nature*, 281: 544), the arabinose promoter system (Guzman et al., (1992) *J. Bacteriol.*, 174: 7716-7728), alkaline phosphatase, a tryptophan (trp) promoter system (Goeddel, (1980) *Nucleic Acids Res.*, 8: 4057 and EP 36,776) and hybrid promoters such as the tac promoter (deBoer et al., (1983) *Proc. Natl. Acad. Sci. USA*, 80: 21-25). However, other known bacterial promoters are suitable. Their nucleotide sequences have been published, thereby enabling a skilled worker operably to ligate them to DNA encoding the polypeptide of interest (Siebenlist et al, (1980) *Cell*, 20: 269) using linkers or adaptors to supply any required restriction sites. See also, e.g., Sambrook et al., supra; and Ausubel et al., supra.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

(v) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., (1977) *Proc. Natl. Acad. Sci. USA*, 74: 5463-5467 or Messing et al., (1981) *Nucleic Acids Res.*, 9: 309, or by the method of Maxam et al., (1980) *Methods in Enzymology*, 65: 499. See also, e.g., Sambrook et al., supra; and Ausubel et al., supra.

The nucleic acid encoding the heparin binding protein of interest is inserted into the host cells. Typically, this is accomplished by transforming the host cells with the above-described expression vectors and culturing in conventional nutrient media modified as appropriate for inducing the various promoters.

Culturing the Host Cells

Suitable prokayotic cells for use to express the heparin binding proteins of interest are well known in the art. Host cells that express the recombinant protein abundantly in the form of inclusion bodies or in the perplasmic or intracellular space are typically used. Suitable prokaryotes include bacteria, e.g., eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcescens*. One example of an *E. coli* host is *E. coli* 294 (ATCC 31,446). Other strains such as *E. coli* B, *E. coli* X1776 (ATCC 31,537), and *E. coli* W3110 (ATCC 27,325) are also suitable. These examples are illustrative rather than limiting. Strain W3110 is a typical host because it is a common host strain for recombinant DNA product fermentations. In one aspect of the invention, the host cell should secrete minimal amounts of proteolytic enzymes. For example, strain W3110 may be modified to effect a genetic mutation in the genes encoding proteins, with examples of such hosts including *E. coli* W3110 strains 1A2, 27A7, 27B4, and 27C7 described in U.S. Pat. No. 5,410,026 issued Apr. 25, 1995. For example, a strain for the production of VEGF is *E. coli* stain W3110 having the genotype tonAΔ ptr3 phoAΔE15 Δ(argF-lac)169 degP41 ilvg designated 49B3. In another example, a strain for the production of VEGF is the *E. coli* strain (62A7) having the genotype ΔfhuA (ΔtonA) ptr3,lacI$^q$, lacL8, ΔompT Δ(nmpC-fepE) ΔdegP ilvG$^+$. See also, e.g., table spanning pages 23-24 of WO2004/092393.

Prokaryotic cells used to produce the heparin binding protein of interest are grown in media known in the art and suitable for culture of the selected host cells, including the media generally described by Sambrook et al., *Molecular Cloning, A Laboratory Manual*, Cold Spring Harbor Laboratory Press (Cold Spring Harbor, N.Y.) (2001). Media that are suitable for bacteria include, but are not limited to, AP5 medium, nutrient broth, Luria-Bertani (LB) broth, Neidhardt's minimal medium, and C.R.A.P. minimal or complete medium, plus necessary nutrient supplements. In certain embodiments, the media also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol, and dithiothreitol.

Examples of suitable media are given in U.S. Pat. Nos. 5,304,472 and 5,342,763. C.R.A.P. phosphate-limiting media consists of 3.57 g $(NH_4)_2(SO_4)$, 0.71 g Na citrate-$2H_2O$, 1.07 g KCl, 5.36 g Yeast Extract (certified), 5.36 g HycaseSF™-Sheffield, adjusted pH with KOH to 7.3, qs volume adjusted to 872 ml with deionized $H_2O$ and autoclaved; cooled to 55° C. and supplemented with 110 ml 1 M MOPS pH 7.3, 11 ml 50% glucose, 7 ml 1 M $MgSO_4$). Carbenicillin may then be added to the induction culture at a concentration of 50 µg/ml.

The prokaryotic host cells are cultured at suitable temperatures. For *E. coli* growth, for example, the temperature ranges from, e.g., about 20° C. to about 39° C., or from about 25° C. to about 37° C., or at about 30° C.

Where the alkaline phosphatase promoter is employed, *E. coli* cells used to produce the polypeptide of interest of this invention are cultured in suitable media in which the alkaline phosphatase promoter can be partially or completely induced as described generally, e.g., in Sambrook et al., *Molecular Cloning, A Laboratory Manual*, Cold Spring Harbor Laboratory Press (Cold Spring Harbor, N.Y.) (2001). The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

If the promoter is an inducible promoter, for induction to occur, typically the cells are cultured until a certain optical density is achieved, e.g., a $A_{550}$ of about 200 using a high cell density process, at which point induction is initiated (e.g., by addition of an inducer, by depletion of a medium component, etc.), to induce expression of the gene encoding the polypeptide of interest.

Any necessary supplements may also be included at appropriate concentrations that would be known to those skilled in the art, introduced alone or as a mixture with another supplement or medium such as a complex nitrogen source. The pH of the medium may be any pH from about 5-9, depending mainly on the host organism. For $E.$ $coli$, the pH is, e.g., from about 6.8 to about 7.4, or about 7.0.

Formulations of Heparin Binding Proteins

The polypeptide recovered, e.g., using the methods described herein, may be formulated in a pharmaceutically acceptable carrier and is used for various diagnostic, therapeutic, or other uses known for such molecules. For example, VEGF described herein can be used in immunoassays, such as enzyme immunoassays. Therapeutic uses for the heparin binding proteins obtained using the methods described herein are also contemplated. For example, a growth factor or hormone, e.g., VEGF, can be used to enhance growth as desired. For example, VEGF can be used to promote wound healing of, e.g., an acute wound (e.g., burn, surgical wound, normal wound, etc.) or a chronic wound (e.g., diabetic ulcer, pressure ulcer, a decubitus ulcer, a venous ulcer, etc.), to promote hair growth, to promote tissue growth and repair (e.g., bone, liver, etc.), etc.

Therapeutic formulations of heparin binding proteins are prepared for storage by mixing a molecule, e.g., a polypeptide, having the desired degree of purity with optional pharmaceutically acceptable carriers, excipients or stabilizers (Remington's *Pharmaceutical Sciences* 18*th edition*, Gennaro, A. Ed. (1995)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In certain embodiments, the formulations to be used for in vivo administration are sterile. This is readily accomplished by filtration through sterile filtration membranes. HBP can be stored in lyophilized form or as an aqueous solution or gel form. The pH of the HBP preparations can be, e.g., from about 5 to 8, although higher or lower pH values may also be appropriate in certain instances. It will be understood that use of certain of the excipients, carriers, or stabilizers can result in the formation of salts of the HBP.

Typically for wound healing, HBP is formulated for site-specific delivery. When applied topically, the HBP is suitably combined with other ingredients, such as carriers and/or adjuvants. There are no limitations on the nature of such other ingredients, except that they must be pharmaceutically acceptable and efficacious for their intended administration, and cannot significantly degrade the activity of the active ingredients of the composition. Examples of suitable vehicles include ointments, creams, gels, sprays, or suspensions, with or without purified collagen. The compositions also may be impregnated into sterile dressings, transdermal patches, plasters, and bandages, optionally in liquid or semi-liquid form.

For obtaining a gel formulation, the HBP formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. In certain embodiments of the invention, the gelling agent herein is one that is, e.g., inert to biological systems, nontoxic, simple to prepare, and/or not too runny or viscous, and will not destabilize the HBP held within it.

In certain embodiments, the polysaccharide is an etherified cellulose derivative, in another embodiment one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. In one embodiment, methylcellulose is the polysaccharide. If methylcellulose is employed in the gel, e.g., it typically comprises about 2-5%, or about 3%, or about 4% or about 5%, of the gel, and the HBP is present in an amount of about 300-1000 mg per ml of gel.

The polyethylene glycol useful for gelling is typically a mixture of low and high molecular weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

The active ingredients may also be entrapped in microcapsules, or sustained-release preparations. See, e.g., Remington's *Pharmaceutical Sciences* 18th edition, Gennaro, A. Ed. (1995). See also Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design The Subunit and Adjuvant Approach,* Powell and Newman, eds, (Plenum Press: New York, 1995), pp. 439-462; WO 97/03692, WO 96/40072, WO 96/07399; U.S. Pat. No. 5,654, 010; DE 3,218,121; Epstein et al., (1985) *Proc. Natl. Acad. Sci. USA,* 82: 3688-3692; Hwang et al., (1980) *Proc. Natl. Acad. Sci. USA,* 77: 40304034; EP 52,322; EP 36,676; EP 88,046; EP 143,949; EP 142,641; Japanese patent application 83-118008; U.S. Pat. Nos. 4,485,045 and 4,544,545; and EP 102,324.

The following examples are offered by way of illustration and not by way of limitation.

EXAMPLES

Example 1

Recombinant Human VEGF Expressed in *Escherichia coli*

Figure 1:
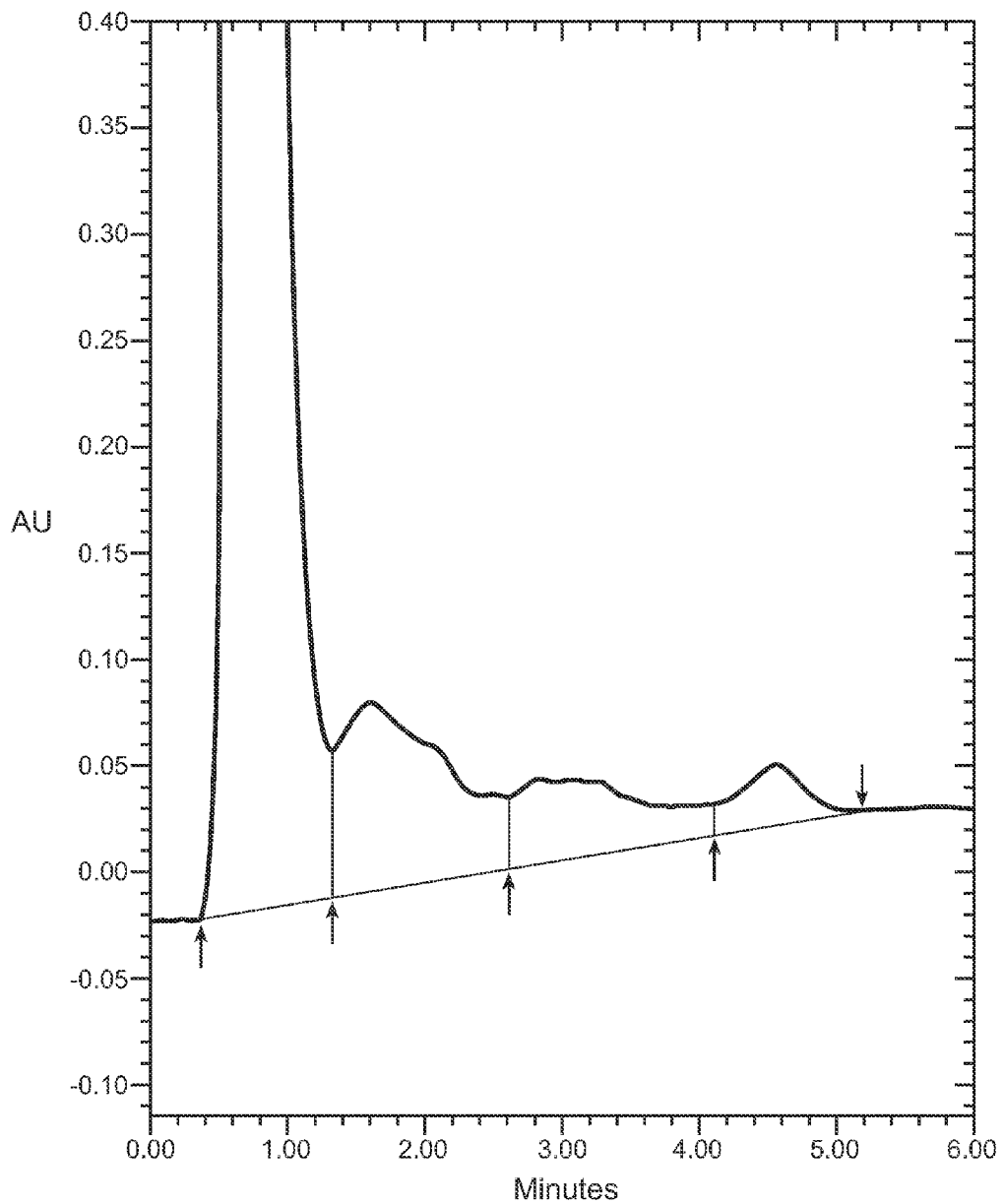
FIG. 1 illustrates a chromatograph from VEGF produced by bacterial strain W3110 loaded on a POROS HE2/M column (4.6×100 mm, PerSeptive BioResearch Products, Cambridge, Mass.). For example, the POROS HE/2 M column is equilibrated in 10 mM sodium phosphate, pH 7 containing 0.15 M sodium chloride. The column is eluted using a linear gradient from 0.15-2 M sodium chloride in, 10 mM sodium phosphate, pH 7 over 10 minutes. The eluant is monitored at 280 nm. The protein recovered in each peak corresponds to VEGF however only peak 3 corresponds to a biologically active properly refolded VEGF.
Figure 2:
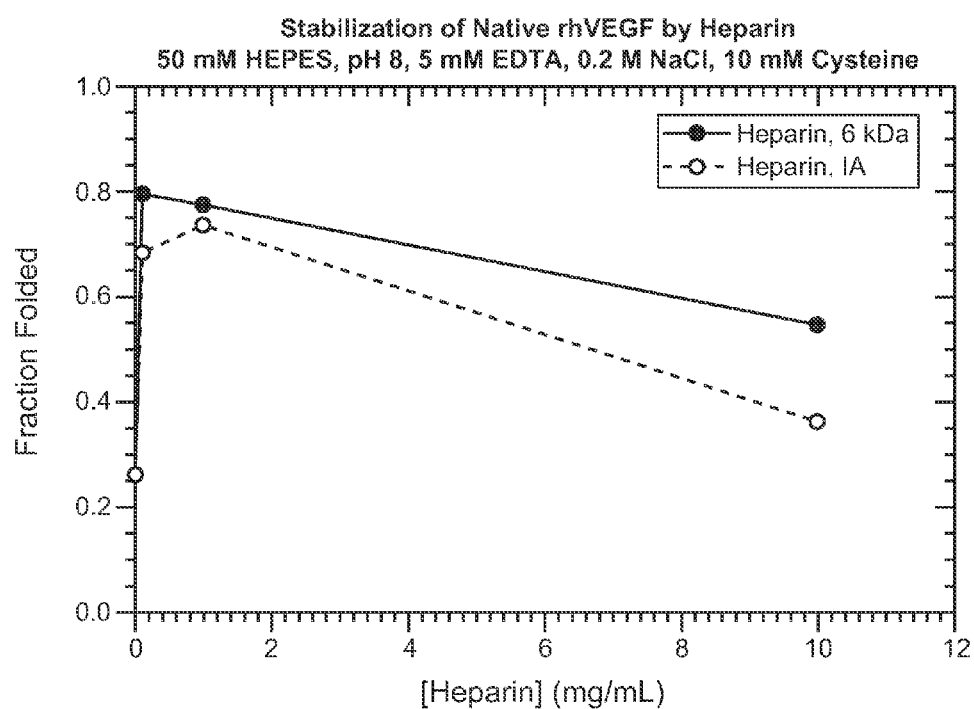
FIG. 2 illustrates a graph depicting the stabilization of native properly folded VEGF by heparin. The VEGF is suspended in 50 mM HEPES, pH 8, containing 5 mM EDTA, 0.2 M NaCl and 10 mM cysteine.
Figure 3A:
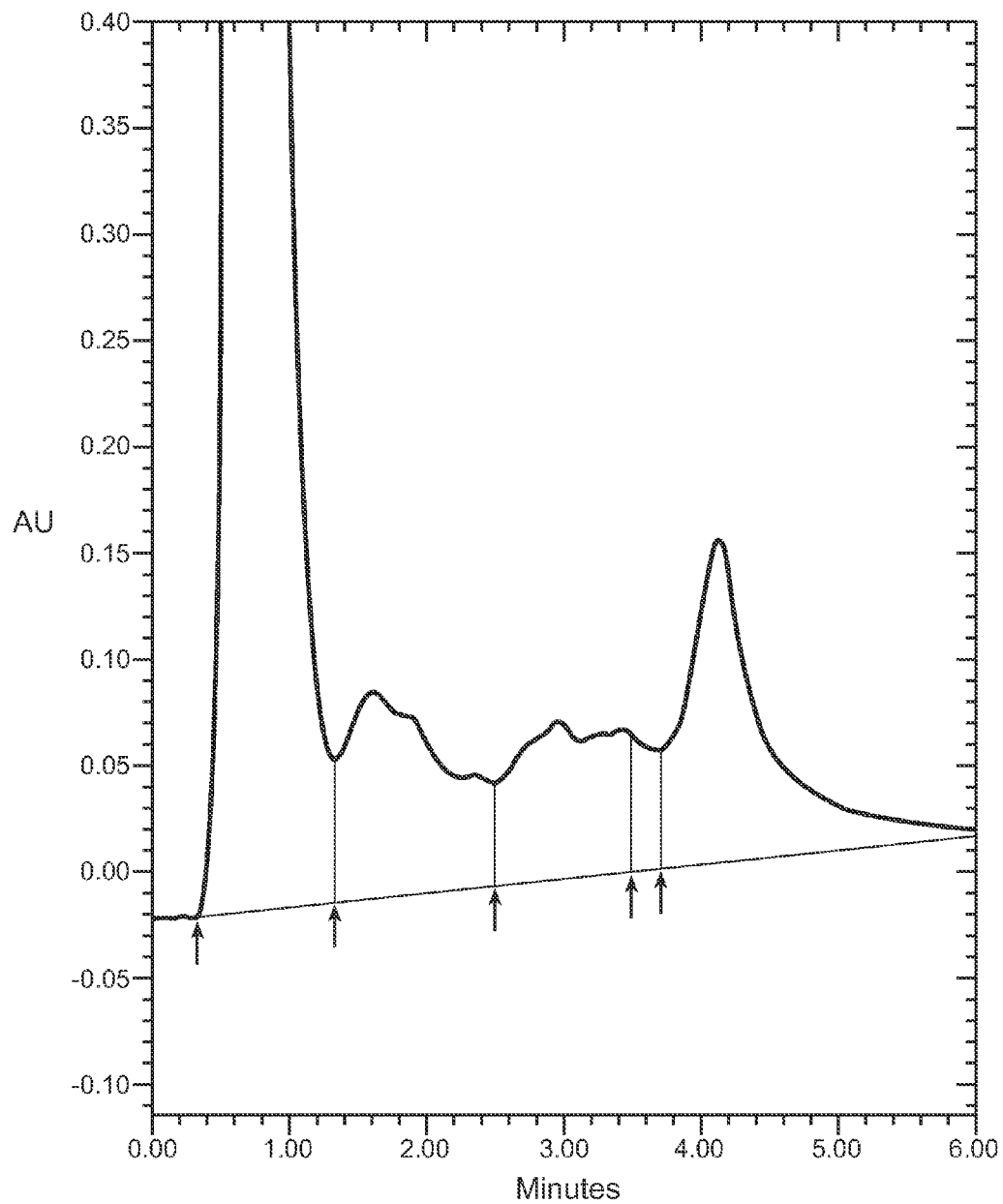
FIGS. 3A-3D illustrates chromatographs from VEGF produced by bacterial strain W3110 and incubated with 12 µg/ml dextran sulfate 5,000 daltons (FIG. 3A); 12 µg/ml dextran sulfate 8,000 daltons (FIG. 3B); 12 µg/ml dextran sulfate 10,000 daltons (FIG. 3C) or 25 µg/ml heparin (FIG. 3D), 3,000 daltons and loaded on a POROS HE2/M column (4.6× 100 mm, PerSeptive BioResearch Products, Cambridge, Mass.). For example, the column is equilibrated in 10 mM sodium phosphate, pH 7 containing 0.15 M sodium chloride. The column is eluted using a linear gradient from 0.15-2 M sodium chloride in, 10 mM sodium phosphate, pH 7 over 10 minutes. The eluant is monitored at 280 nm. The protein recovered in each peak corresponds to VEGF however only peak 3 corresponds to a biologically active properly refolded VEGF.
Figure 3B:
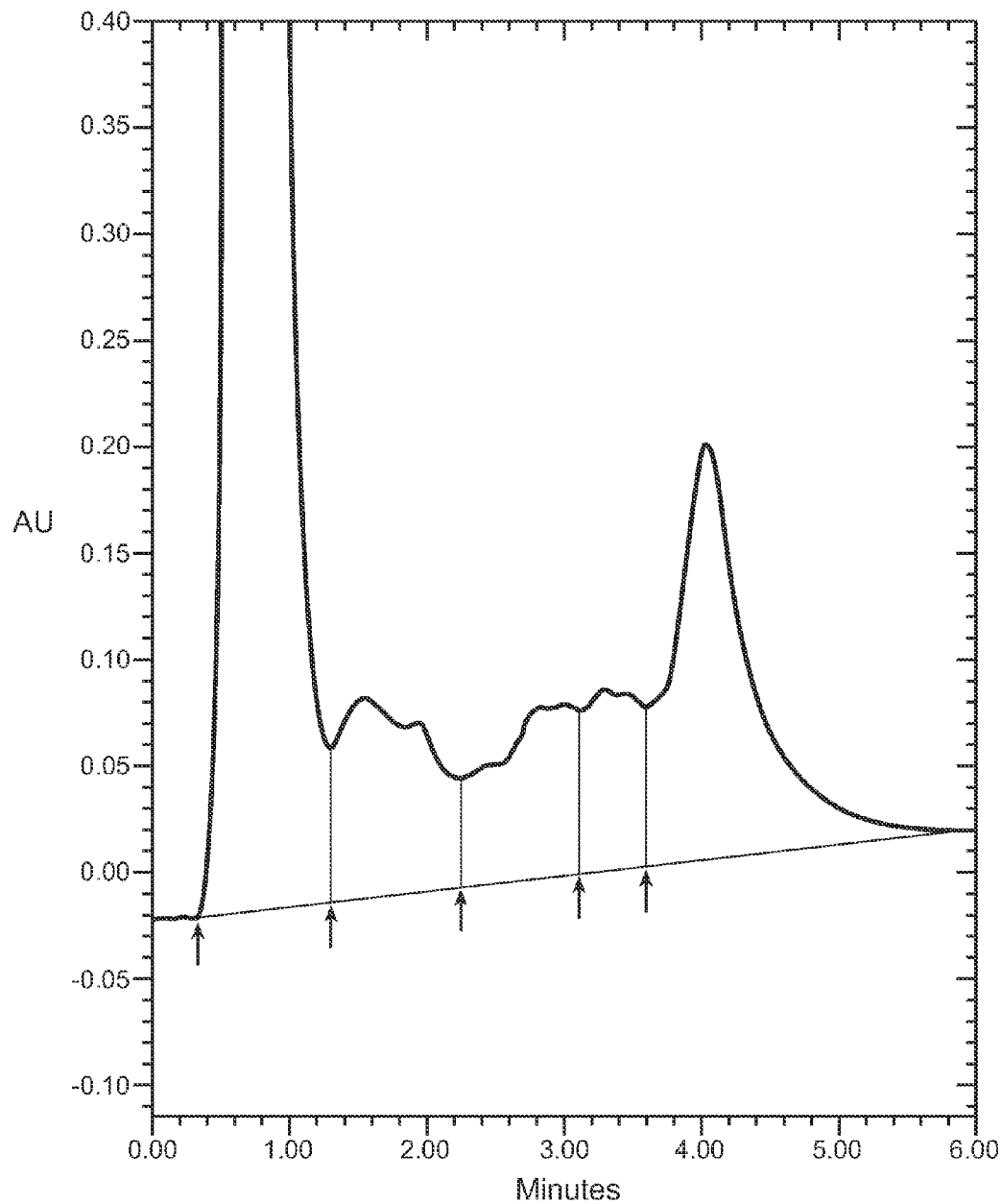
Figure 3C:
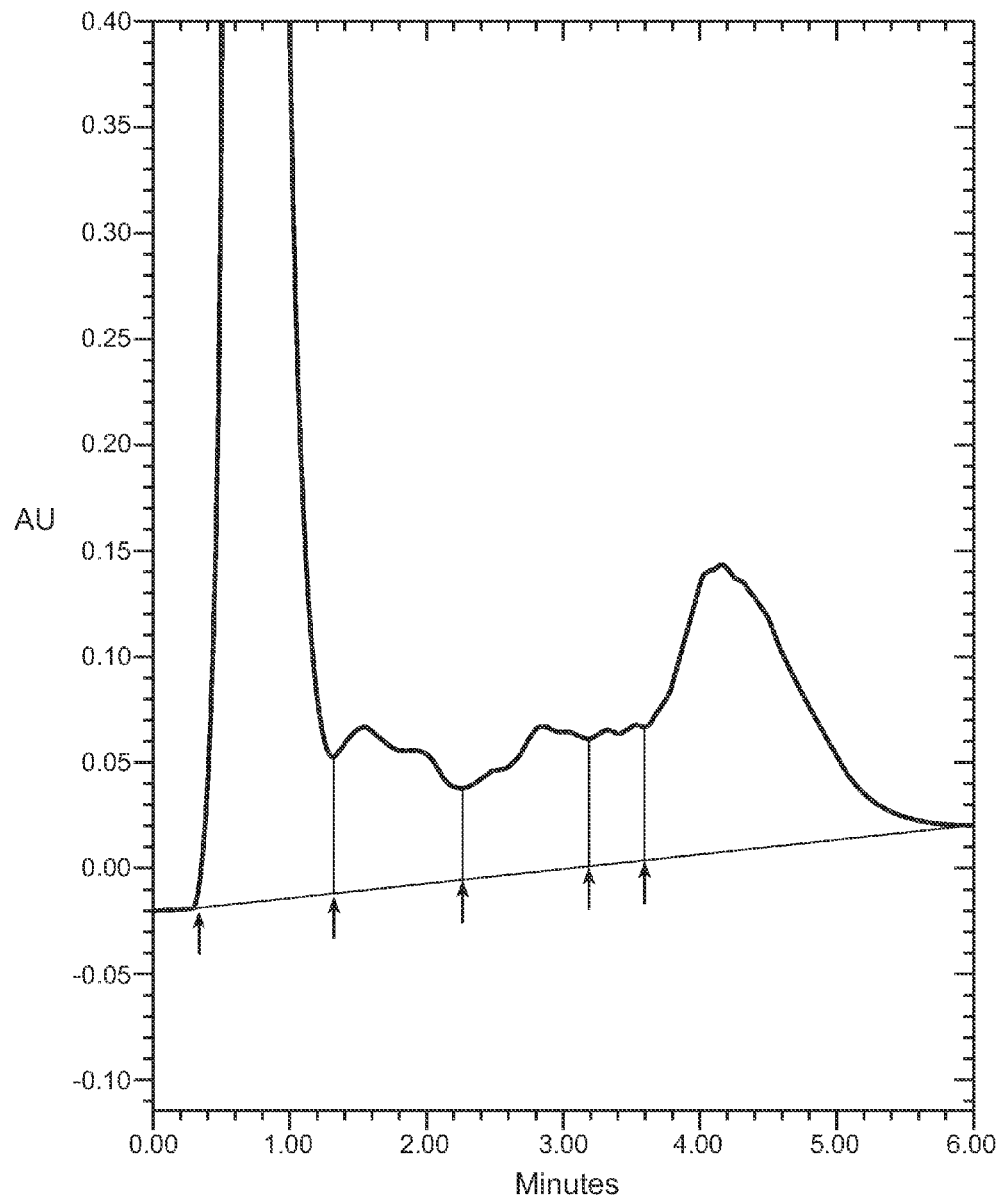
Figure 3D:
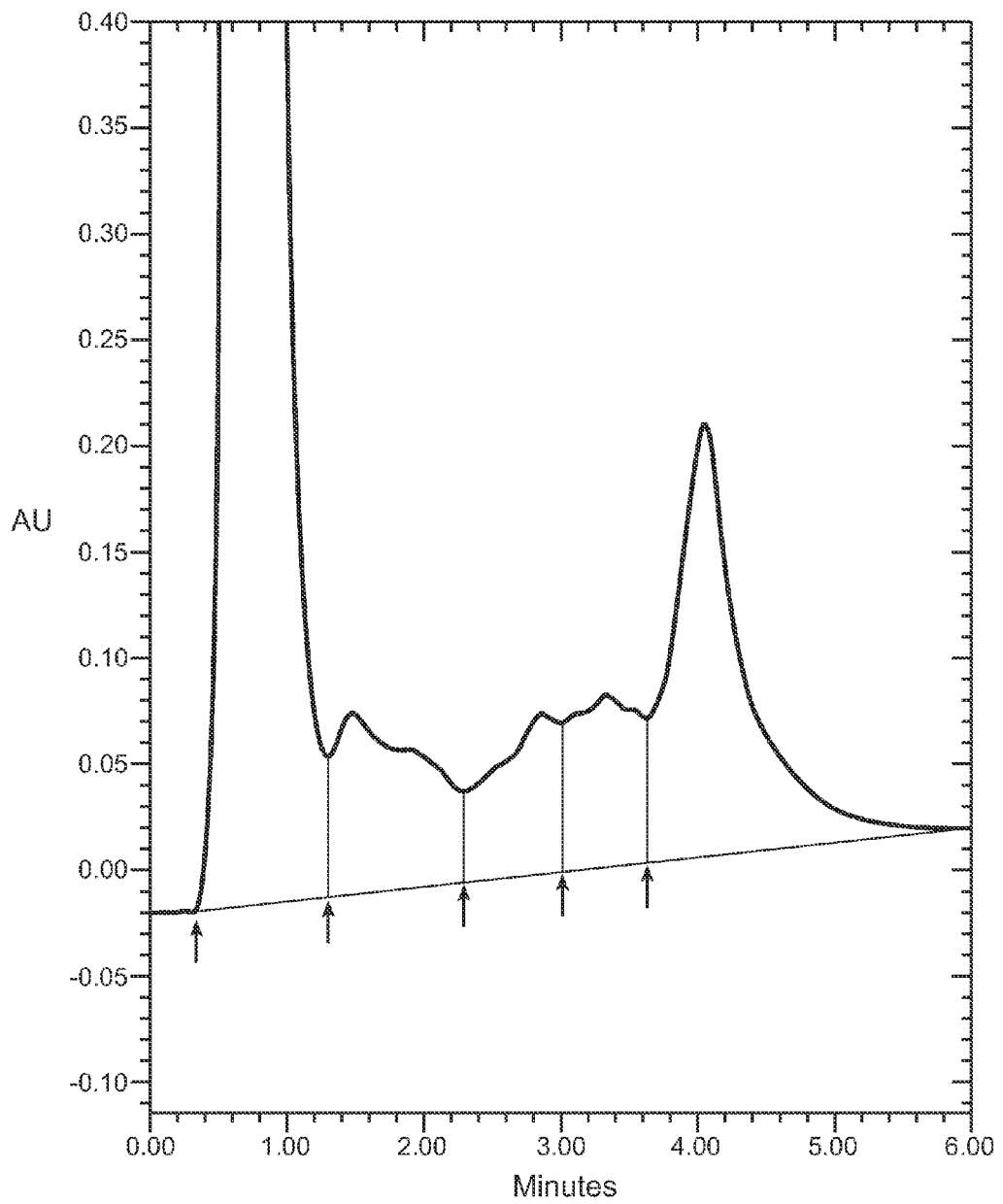

Recombinant human VEGF was expressed in *Escherichia coli.* During synthesis, the protein was secreted into the periplasmic space and accumulated as refractile bodies. Studies were therefore conducted to achieve extraction and refolding of the protein. These studies revealed at least 3 species of VEGF (FIG. 1) were isolated using standard recovery techniques without the addition of a polyanionic agent. Studies with native VEGF showed that heparin addition increased resistance to chaotrope- and thiol-induced denaturation (FIG. 2). In addition, heparin significantly increased the amount of properly refolded VEGF in small scale refolding experiments. To adapt this result to a large-scale process, conditions were discovered which allowed for refolding VEGF in the presence of dextran sulfate, a molecule structurally analagous to heparin. Addition of dextran sulfate improved yields of properly folded biologically active VEGF 3-5-fold relative to controls.

Methods

Plasmid for $VEGF_{165}$ expression—The plasmid pVEGF171 was designed for the expression of human $VEGF_{165}$ (see, e.g., Leung et al., (1989) *Science,* 246:1306-1309) in the *E. coli* periplasm. Transcription of the VEGF coding sequence was placed under tight control of the alkaline phosphatase (AP) promoter (see, e.g., Kikuchi et al., (1981) *Nucleic Acids Research,* 9:5671-8), while sequences required for translation initiation were provided by the trp Shine-Dalgarno region (see, e.g., Yanofsky et al., (1981) *Nucleic Acids Research,* 9:6647-68). The VEGF coding sequence was fused downstream of the bacterial heat-stable enterotoxin II (STII) signal sequence (see, e.g., Lee et al., (1983) *Infect. Immun.* 42:264-8; and, Picken et al., (1983) *Infect. Immun.* 42:269-75) for subsequent secretion into the *E. coli* periplasm. Codon modifications in the STII signal sequence provided for an adjusted translation level, which resulted in an optimal level of VEGF accumulation in the periplasm (see, e.g., Simmons and Yansura, (1996) *Nature Biotechnoloy,* 14:629-34). The lambda to transcriptional terminator (see, e.g., Scholtissek and Grosse, (1987) *Nucleic Acids Research* 15:3185) was located downstream of the VEGF translational termination codon. The replication origin, and both ampicillin and tetracycline resistance genes, were provided by the plasmid pBR322. See, e.g., Bolivar et al., (1977) *Gene* 2:95-113.

Cell Homogenization and Refractile body preparation—Harvested *Escherichia coli* cells were frozen and stored at −70C°. Cells were harvested by BTUX (centrifuge, Alfa laval) centrifugation and freezing using BEPEX (freezer at large scale). Cells were suspended in 5 volumes of 50 mM HEPES/150 mM NaCl/5 mM EDTA pH 7.5 (5 L/kg pellet) and homogenized in a model 15 M laboratory homogenizer Gaulin 15M (small scale) or M3 (large scale) (Gaulin Corporation, Everett, Mass.). The cell suspension was then diluted with an equal volume of the same buffer and refractile bodies were harvested by centrifugation in a BTPX 205 (Alfa Laval Separation AB (Tumba, Sweden) continuous feed centrifuge. Intermediate scale centrifuge used SA1. Alternatively, cells can be homogenized and the pellet can be harvested directly without freezing in BEPEX and rehydrating.

Example II

Extracting and Refolding of Recombinant Human VEGF Expressed in *Escherichia coli*-I Methods Extraction and Refolding—The refractile pellet was suspended in extraction buffer containing 7 M Urea/50 mM HEPPS/pH 8 (final concentration) at 5 L of buffer/kg pellet. Solid dithiothreitol was then added at 3.7 g/kg pellet for a final concentration of 4 mM. See, e.g., FIG. 9 for the effect of urea and DTT on extraction of VEGF. The suspension was thoroughly mixed for 1-2 h at 20° C. The pH may be adjusted with 50% sodium hydroxide (w/w) to pH 8.0. Refolding was initiated by addition of 19 volumes of refolding buffer per volume of extraction buffer. The refolding buffer contained 50 mM HEPPS/1 M-2 M Urea/2-5 mM cysteine/0.05%-0.2% TRITON™ X100/pH 8, final concentration. See, e.g., FIG. 10 for the effect of urea and DTT concentration present during refolding. Dextran sulfate, heparin or sodium sulfate was added as indicated. Refold incubation was conducted at room temperature for 4-24 hours. Optionally, the incubation can be conducted at room temperature for up to about 48 hours. The folding was monitored by SDS-PAGE and/or Heparin HPLC. The product was clarified by depth filtration with a Cuno 90SP filter followed by 0.45 µm filtration.

Heparin-binding HPLC Assay—The quality and quantity of properly refolded VEGF was determined using a column containing immobilized heparin. The column POROS HE2/M (4.6×100 mm, HE2/M by PerSeptive BioResearch Products, Cambridge, Mass.) was equilibrated in 10 mM sodium phosphate, pH 7 containing 0.15 M sodium chloride. At a flow rate of 1 mL/min or 2 ml/min, the columns were eluted using a linear gradient from 0.15 M to 2 M sodium chloride in equilibration buffer over 10 min. In some assays, elution was done in 16 min. The eluant was monitored at 280 nm. Typically, the majority of protein was eluted in the void volume and 3 classes of VEGF could be identified. The highest affinity, latest-eluting species was identified as correctly folded VEGF and was subsequently identified as "Peak 3 VEGF".

Results

Heparin protects VEGF against cysteine-mediated denaturation—Addition of 10 mM cysteine to native VEGF resulted in a large decrease in the properly-folded molecule (FIG. 2). This denaturation was prevented by the addition of 2 different forms of heparin at concentrations as low as 20 mM.

TABLE Ia

The Effect of Heparin and Dextran sulfate on VEGF Refolding

| Addition | Concentration (µg/ml) | | | | | | % Increase | or Fold Increase |
|---|---|---|---|---|---|---|---|---|
|  | 0 | 10 | 55 | 100 | 200 | 400 |  |  |
| None | 5.3* |  |  |  |  |  | — | — |
| Low (3 kd) MW heparin |  | 12.2 | 14.2 | 14.8 | 14.1 |  | 179% | 2.8 |
| High MW (6 kD) heparin |  | 15.3 | 16.6 | 13.9 | 15.3 |  | 213% | 3.1 |
| Dextran sulfate (10 Kd) |  | 15.9 | 15.4 | 13.6 | 7.4 | 8.3 | 191% | 2.9 |

Values in the table are the amount of Peak 3 VEGF formed (in mg) per g of refractile pellet. Concentration of each addition is as indicated.
*Average control (5.6 + 5.0 = 5.3)

TABLE Ib

The Effect of Sodium Sulfate on VEGF Refolding

| Addition | Concentration (µg/ml) | | | | | % Increase | or Fold Increase |
|---|---|---|---|---|---|---|---|
|  | 0 | 50 | 98 | 195 | 293 | 455 |  |  |
| None | 5.3 |  |  |  |  |  | — | — |
| sodium sulfate |  | 6.9 | 9.1 | 10.4 | 10.9 | 10.4 | 106% | 2.1 |

Values in the table are the amount of Peak 3 VEGF formed (in mg) per g of refractile pellet. Concentration of sodium sulfate is as indicated

TABLE II

The Effect of Heparins and Dextran sulfates on VEGF Refolding

| Addition | Concentration (µg/ml) | | | | | % Increase | or Fold Increase |
|---|---|---|---|---|---|---|---|
|  | 0 | 2.5 | 12.5 | 50 | 100 |  |  |
| None | 2.2 |  |  |  |  | — | — |
| dextran sulfate (5 Kd) |  | 10.1 | 13.7 | 13.4 | 11.2 | 523% | 6.2 |
| dextran sulfate (8 Kd) |  | 9.9 | 17.2 | 14.0 | 12.9 | 682% | 7.8 |
| dextran sulfate (10 Kd) |  | 13.8 | 19.2 | 14.6 | 10.1 | 773% | 8.7 |
| Low MW (3 Kd) Heparin |  | 10.4 | 16.9 | 14.7 |  | 668% | 7.7 |
| High MW (6 Kd) Heparin |  | 14.1 | 18.8 | 20.2 |  | 818% | 9.2 |

Values in the table are the amount of Peak 3 VEGF formed (in mg) per g of refractile pellet.

SUMMARY

Figure 5:
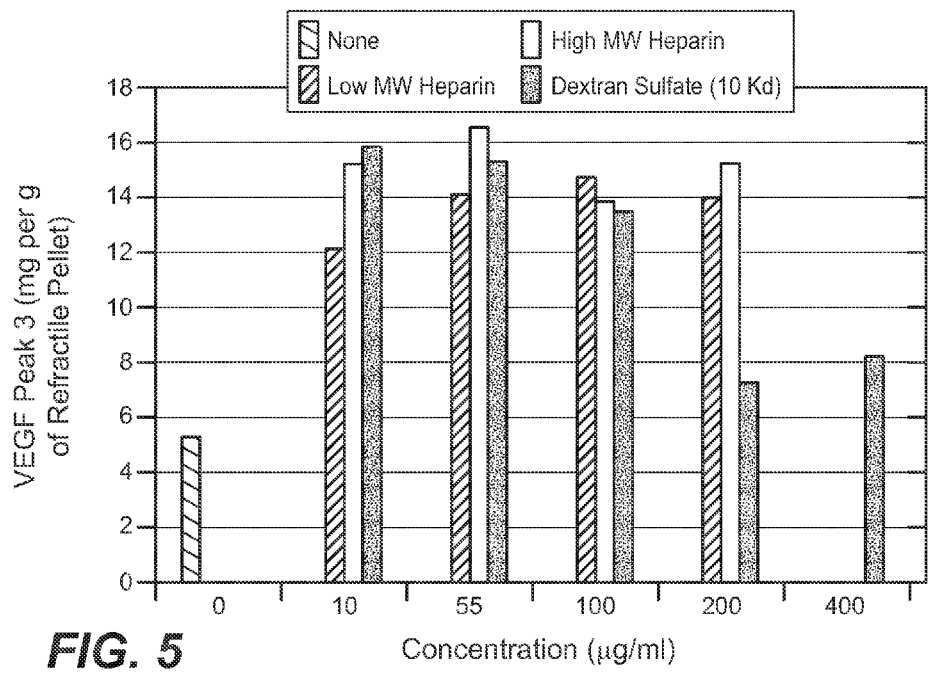
FIG. 5 illustrates the effect of heparin, low molecular weight (MW) and high MW, and dextran sulfate, 10,000 daltons, on VEGF refolding. Peak 3 corresponds to a biologically active properly refolded VEGF.
Figure 6:
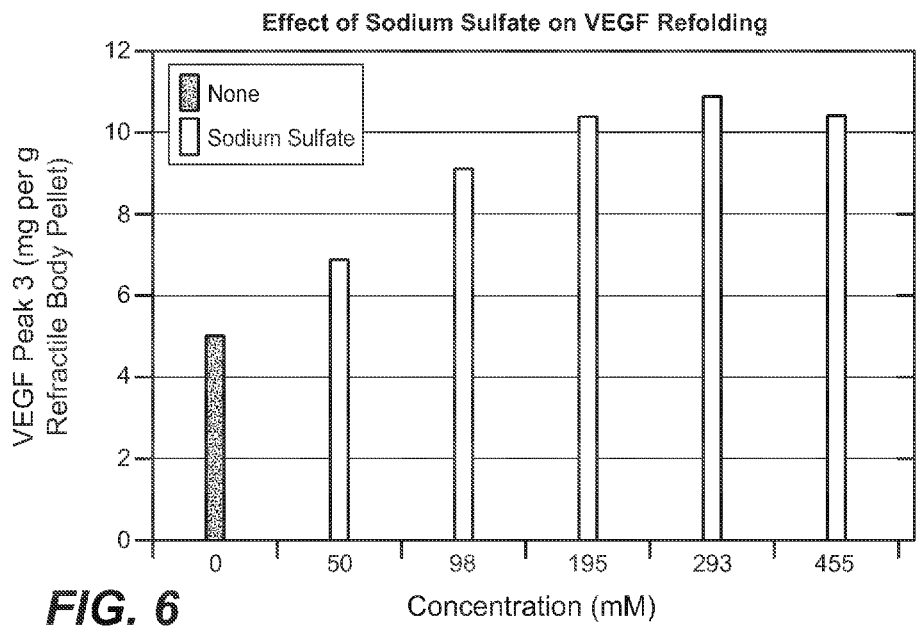
FIG. 6 illustrates the effect of sodium sulfate on VEGF refolding. Peak 3 corresponds to a biologically active properly refolded VEGF.
Figure 7:
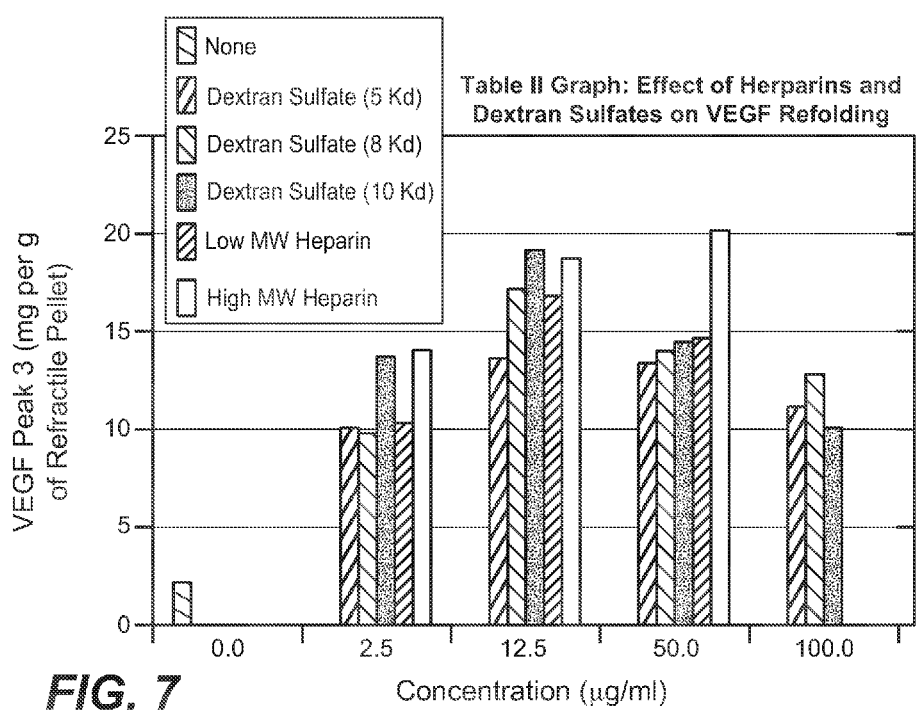
FIG. 7 illustrates the effect of heparin, low molecular weight (MW) and high MW, and dextran sulfate, 5,000 daltons, 8,000 daltons, and 10,000 daltons, on VEGF refolding. Peak 3 corresponds to a biologically active properly refolded VEGF.
Figure 8:
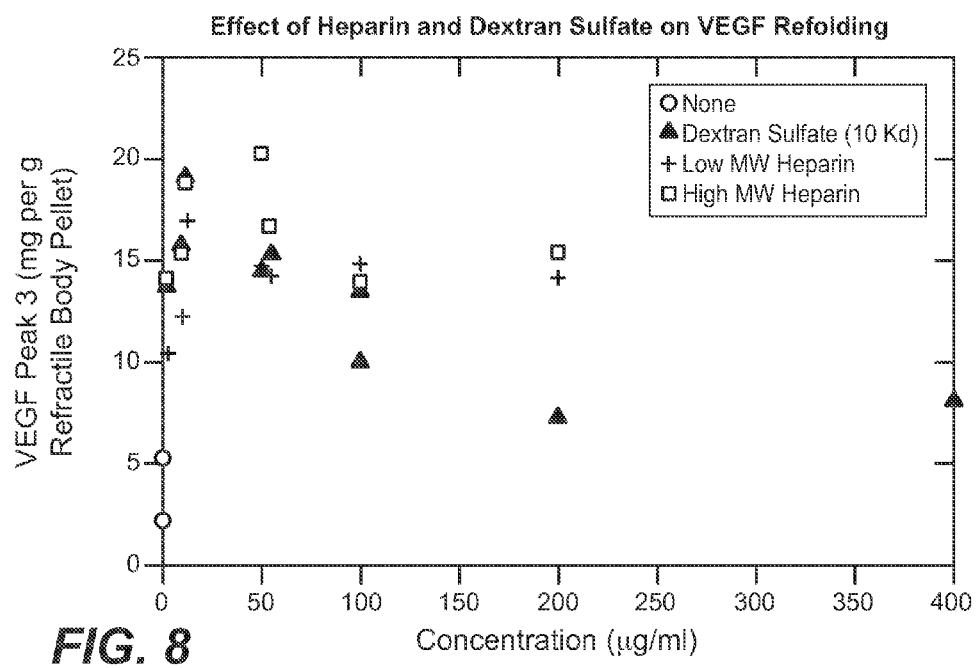
FIG. 8 illustrates the effect of heparin and dextran sulfate on VEGF refolding. Peak 3 corresponds to a biologically active properly refolded VEGF.

Heparin and dextran sulfate increase refolding yields—Due to the protective properties against denaturation described above, the effect of several different forms of sulfated polymers on refolding VEGF was investigated. As seen in TABLE Ia (and in FIG. 5), both low and high molecular weight forms of heparin increased the yield of refolded VEGF approximately 3-fold. As seen in TABLE Ib (and in FIG. 6), sodium sulfate increased the yield of refolded VEGF by approximately 2-fold. The 10 Kd form of dextran sulfate was also effective at increasing refold yields; however, the higher concentration range investigated lead to substrate inhibition. Further investigation demonstrated that 5 Kd, 8 Kd and 10 Kd forms of dextran sulfate all significantly increased the yield of VEGF on refolding (TABLE II). See FIG. 7. See also FIG. 8.

Example III

Effect of Different Buffers and TRITON™ X-100 on the Recovery of VEGF

Results

| Buffer | VEGF (mg/g pellet) |
|---|---|
| HEPES, pH 8 | 13.3 |
| HEPES, pH 8 with TRITON ™ | 14.3 |
| HEPPS, pH 8 | 16.6 |
| TrisHCl, pH 8 | 12.8 |
| HEPES, pH 7.2 | 9.1 |
| HEPPS, pH 7.2 | 10.7 |
| HEPES, pH 8 | 10.3 |
| HEPPS, pH 8 | 12.8 |
| HEPES, pH 8 + TRITON ™ X-100 | 12.4 |
| HEPPS, pH 8 + TRITON ™ X-100 | 13.9 |

SUMMARY

The combined data of Example I, II and III demonstrate a significant (2-5 fold) improvement in yield by including either heparin sulfates or dextran sulfates when refolding VEGF, a heparin-binding growth factor as well as the conditions of recovery. This method has been implemented successfully at industrial scale. It is expected that that this method is applicable in the refolding of other basic growth factors and other proteins that bind heparin.

Example IV

Figure 12:
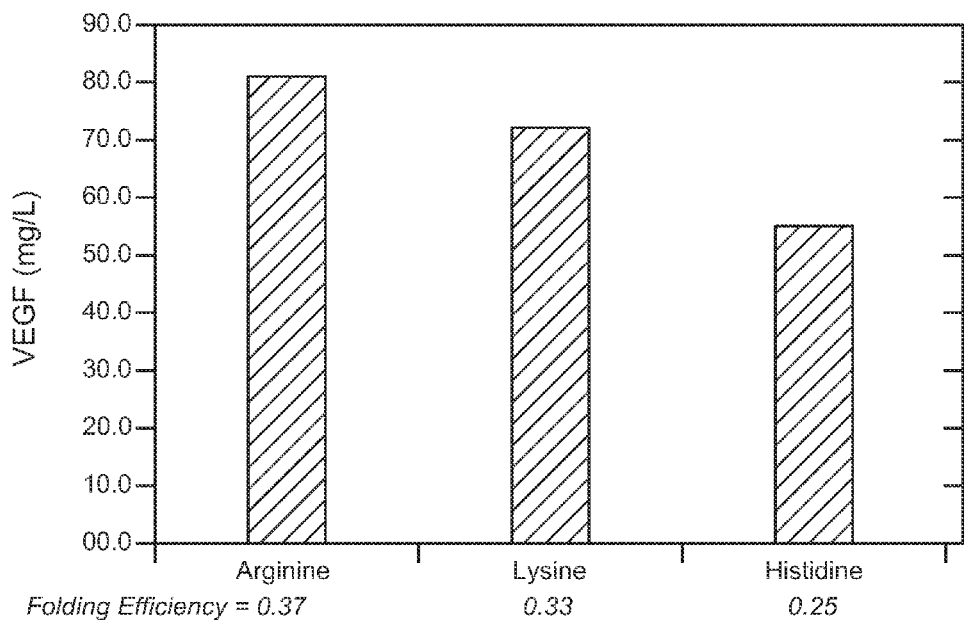
FIG. 12 illustrates the effect of the presence of charged amino acids. At 0.75 M concentration in the second buffered solution both arginine and lysine are beneficial whereas histidine has little additive effect as compared to the buffered solution without it. Additionally arginine has been shown to have similar effect at concentrations of 0.1 to 1 M.

Extracting and Refolding of Recombinant Human VEGF Expressed in *Escherichia coli*-II Methods Extraction and Refolding—The refractile pellet was suspended in extraction buffer where the final concentration was 7 M Urea, 2-30 mM DTT (e.g., 10 mM DTT), 50 mM HEPPS/pH 7-9 (e.g., pH 8) at 5 L of buffer/kg pellet. The suspension was thoroughly mixed for 1-2 h at room temperature. Refolding was initiated by addition of 19 volumes of refolding buffer per volume of extraction buffer. The refolding buffer contained as the final concentration 1 M or 1.3 M urea, 2-15 mM cysteine (e.g., 7.5 mM cysteine), 0.5 mM DTT, 0-0.75 M arginine (e.g., 100 mM arginine), 15 mg/L dextran sulfate, 50 mM HEPPS, 0.05% TRITON™ X100/pH 8. See, e.g., FIG. 12 for the effect on refolding in the presence of charged amino acids, where the addition of histidine produced the same effect as without amino acid additives. Refold incubation was conducted at room temperature for 12-24 hours. Optionally, the incubation can be conducted at room temperature for up to about 48 hours. Optionally, air or oxygen can be added during the refolding process (0.3-1 cc/min/L). The folding was monitored by SDS-PAGE and/or Heparin HPLC. The product was clarified by depth filtration with a Cuno 90SP filter followed by 0.45 μm filtration.

Figure 13:
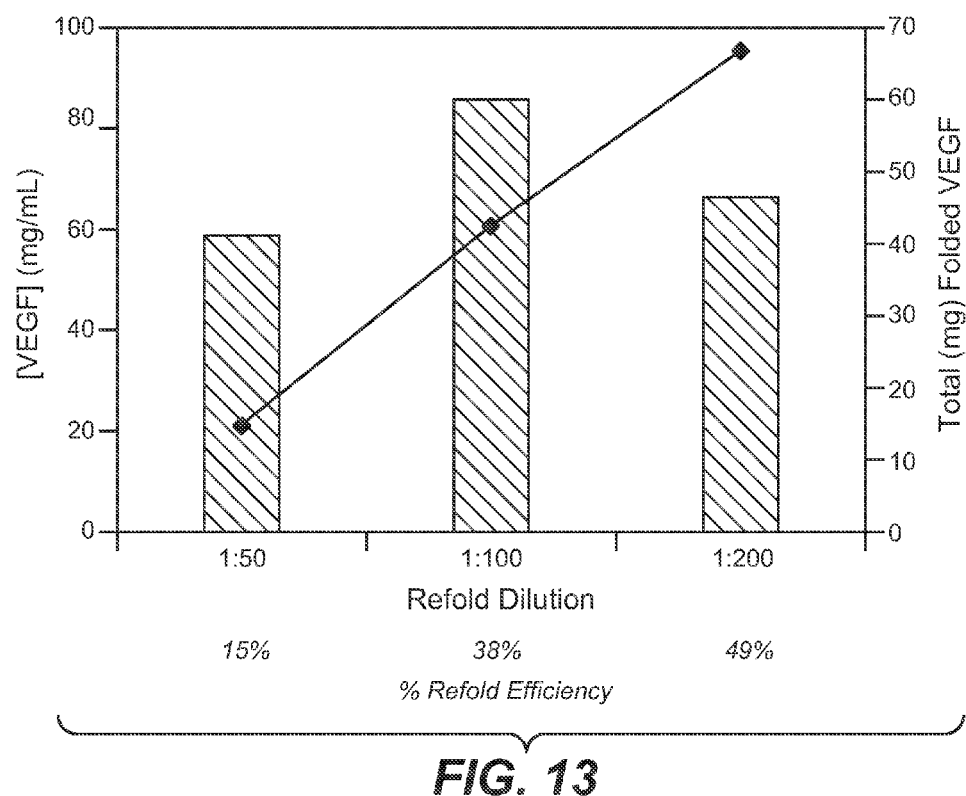
FIG. 13 illustrates the effect of dilution in the % refold efficiency, where, although the total VEGF concentration is lower as the dilution increases, the % refold efficiency is higher with more dilution.

The overall dilution of the extraction and refolding steps was 1:100. Increasing the overall dilution of the extraction and refolding steps, e.g., to 1:100 to 1:200, increased the total amount of active VEGF although the concentration is lower. See FIG. 13.

The efficiency of refolding can be determined by determining the amount of dimer/monomer, where monomers can be determined by a C18 reverse-phase HPLC column and dimer formation can be determined by heparin column chromatography or SP-5PW cation exchange chromatography assay.

Example V

Large-Scale Refolding

In order to test the scalability of the optimized refolding conditions, studies were conducted to examine the kinetics of refolding at small (0.1 L), intermediate (1 L) and pilot plant (250 L to 400 L) scale. As shown in FIG. 4, the kinetics of refolding at large scale were indistinguishable from the smaller scales and the final titer of refolded VEGF was slightly increased. These data demonstrate the scalablility of refolding with dextran sulfate. The product was further clarified by depth filtration with a Cuno 90SP filter followed by 0.45 μm filtration.

Example VI

Purification I of rhVEGF after Refolding

MacroPrep Ceramic Hydroxyapatite Chromatography—After refolding, insoluble material in the pool was removed by depth filtration. The clarified pool was then loaded on to a ceramic hydroxyapatite column (35D×31H=30L) (Bio Rad, Hercules, Calif.) equilibrated in 50 mM HEPPS/0.05% TRITON™ X100/pH 8. The non-binding protein was removed by washing with equilibration buffer and the VEGF eluted using an isocratic step of 50 mM HEPPS/0.05% TRITON™ X100/0.15 M sodium phosphate/pH 8. The flow rate was 120 cm/hr. Pooling fractions were determined by Heparin HPLC analysis of fractions.

Butyl SEPHAROSE™ Fast Flow Chromatography—The pool of VEGF was loaded onto a column of Butyl SEPHAROSE™ Fast Flow (35 D×26 H=25L) (GE Healthcare, Uppsala, Sweden) equilibrated in 50 mM HEPPS/0.05% TRITON™ X100/0.15 M sodium phosphate/pH 8. The flow rate was 100 cm/hr. The column was washed with equilibration buffer and the VEGF collected in the column effluent. Fractions were collected and protein containing fractions were pooled, by measuring A280 nm.

Macro Prep High S Chromatography—The Butyl SEPHAROSE™ pool was loaded onto a column of Macro Prep High S (30D×39 H=27 L) (BioRad, Hercules, Calif.) that was equilibrated in 50 mM HEPES/pH 8. After washing the effluent absorbance at 280 nm to baseline, the column was washed with two column volumes of 50 mM HEPES/0.25 M sodium chloride/pH 8. The VEGF was eluted using a linear, 8-column-volume gradient from 0.25-0.75 M sodium chloride in 50 mM HEPES/pH 8. The flow rate was 75-200 cm/hr. Fractions were collected and those which contained properly-folded VEGF, as determined by a heparin-binding assay, e.g., Heparin HPLC, were pooled.

Phenyl 5PW TSK Chromatography—The Macro Prep High S pool was conditioned with an equal volume of 50 mM HEPES/0.8 M sodium citrate/pH 7.5. The conditioned pool was then loaded on to a column of Phenyl 5PW TSK (18 D×43 H=11 L) (Tosohaas, Montgomeryville, Pa.) that was equilibrated with 50 mM HEPES/0.4 M sodium citrate/pH 7.5. After washing non-binding protein through the column with equilibration buffer, the VEGF was eluted from the column using a 10-column-volume gradient from 0.4-0 M sodium citrate in 50 mM HEPES, pH 7.5. Fractions were assayed by SDS-polyacrylamide gel electrophoresis and those containing VEGF of sufficient purity were pooled.

Ultrafiltration/Diafiltration—The pooled VEGF was ultrafiltered on a 5 kD regenerated cellulose membrane (G30619); Unit Pellicon; Feed Rate 17.1 L/min. The membrane was conditioned with polysorbate 20. The pooled VEGF was ultrafiltered at a concentration of 6 g/L (UF1). The sample was diafiltrated with 7-14 DV (Diavolume) with 5 mM Sodium Succinate/275 mM Trehalose/pH 5.0. The final formulation was 5 mM Sodium Succinate/275 mM Trehalose/0.01% polysorbate 20/pH5.0, at a concentration of 5 mg/ml.

Example VII

Purification II of rhVEGF after Refolding

Cation Exchange Liquid Chromatography—After refolding, insoluble material in the pool can be removed by depth filtration. The refold pool is conditioned to pH 5.0-7.5 and about 2 to 6.5 mS/cm. In one embodiment, the pool is conditioned to pH 6.5 and 5 mS/cm. The refold pool can be then loaded on to a sulfopropyl extreme load column (SPXL) and eluted using a gradient of increasing salt concentration. Pooling fractions can be determined by Heparin HPLC analysis of fractions.

Hydrophobic Interaction Column (HIC):—The SPXL elution pool of VEGF can be conditioned to 50 mS/cm for loading onto a Phenyl TSK chromatography column (Tosohaas, Montgomeryville, Pa.). Fractions are collected and protein containing fractions are pooled.

IEX or Mixed Mode:—The Phenyl TSK pool can be loaded onto a column of ion exchange chromatography (IEX) or mixed-mode chromatography. Fractions are collected and those which contained properly-folded VEGF, as determined by assays described herein are pooled.

Ultrafiltration/Diafiltration—The pooled VEGF can be ultrafiltered on a 5 kD regenerated cellulose membrane (G30619); Unit Pellicon; Feed Rate 17.1 L/min. For example, the membrane is conditioned with polysorbate 20. The pooled VEGF is ultrafiltered at a concentration of 6 g/L (UF1). The sample is diafiltrated with 7-14 DV (Diavolume) with 5 mM Sodium Succinate/275 mM Trehalose/pH 5.0.

In methods and processes described herein, final purity and/or activity can be assessed by peptide mapping, disulfide mapping, SDS-PAGE (both reduced and non-reduced), circular dichroism, limulus amobocyte lysate (LAL), heparin chromatography, heparin HPLC (e.g., Heparin HPLC can be used to determine VEGF dimer concentration), reverse phase (rp) HPLC chromatography (e.g., rpHPLC can be used to determine VEGF monomer concentration), heparin binding, receptor binding (for example for VEGF e.g., KDR receptor binding-Bioanalytic R&D, and/or Flt1 receptor binding), SEC Analysis, cell assays, HUVEC potency assays, ELISAs with VEGF antibodies, mass spec analysis, etc.

It is understood that the deposits, examples and embodiments described herein are for illustrative purposes only and that various modifications or changes in light thereof will be suggested to persons skilled in the art and are to be included within the spirit and purview of this application and scope of the appended claims. All publications, citations, patents, and patent applications cited herein are hereby incorporated by reference in their entirety for all purposes.

What is claimed is:

1. A process for recovering a heparin binding protein from a prokaryotic cell culture, wherein said heparin binding protein is vascular endothelial growth factor (VEGF), the process comprising the steps of
   (a) isolating said heparin binding protein from the periplasm of said prokaryotic cell culture;
   (b) denaturing said isolated heparin binding protein in a first buffered solution comprising a chaotropic agent and a reducing agent;
   (c) incubating said denatured heparin binding protein in a second buffered solution comprising a chaotropic agent and a sulfated polyanionic agent, wherein said sulfated polyanionic agent is dextran sulfate or sodium sulfate, for such a time and under such conditions that refolding of the heparin binding protein occurs; and
   (d) recovering said refolded heparin binding protein, wherein there is about a 2- to 5-fold increase in refolded heparin binding protein recovered compared to incubating with no sulfated polyanionic agent.

2. The process of claim 1, wherein the VEGF is $VEGF_{165}$.

3. The process of claim 1, wherein the dextran sulfate is between about 3,000 daltons and 10,000 daltons.

4. The process of claim 3, wherein the dextran sulfate is between about 8,000 and 10,000 daltons.

5. The process of claim 1, wherein said first and second buffered solutions comprise HEPPS pH 8.0.

6. The process of claim 1, wherein said second buffered solution further comprises a reducing agent.

7. The process of claim 6, wherein the reducing agent of the second buffered solution comprises a combination of cysteine and DTT.

8. The process of claim 1, wherein said second buffered solution further comprises a nonionic detergent.

9. The process of claim 1, wherein said second buffered solution further comprises arginine and/or lysine.

10. The process of claim 1, wherein said recovery step (d) comprises sequentially contacting said refolded heparin binding protein to a hydroxyapatite chromatographic support, a first hydrophobic interaction chromatographic support; a cationic chromatographic support, and a second hydrophobic interaction chromatographic support, and selectively eluting the heparin binding protein from each support.

11. The process of claim 10, wherein said first and second hydrophobic interaction chromatographic support is selected from the group consisting of butyl-, propyl-, octyl- and aryl-agarose resins.

12. The process of claim 10, wherein said first hydrophobic interaction chromatographic support is a butyl-agarose support and said second hydrophobic interaction chromatographic support is a phenyl-agarose support resin.

13. The process of claim 1, wherein said recovery step (d) comprises sequentially contacting said refolded heparin binding protein to a cation exchange support; a hydrophobic interaction chromatographic support, and an ion exchange chromatographic support, and selectively eluting the heparin binding protein from each support.

14. A method for recovering a heparin binding protein from a prokaryotic cell culture, wherein said heparin binding protein is VEGF, the method comprising the steps of
(a) isolating said heparin binding protein from the periplasm of said prokaryotic cell culture;
(b) denaturing said isolated heparin binding protein in a first buffered solution comprising a chaotropic agent and a reducing agent;
(c) incubating said denatured heparin binding protein in a second buffered solution comprising a chaotropic agent and a sulfated polyanionic agent, wherein said sulfated polyanionic agent is dextran sulfate or sodium sulfate, for such a time and under such conditions that refolding of the heparin binding protein occurs, wherein there is about a 2- to 5-fold increase in refolded heparin binding protein recovered compared to incubating with no sulfated polyanionic agent; and
(d) sequentially contacting said refolded heparin binding protein with a hydroxyapatite chromatographic support, a first hydrophobic interaction chromatographic support, a cationic chromatographic support, and a second hydrophobic interaction chromatographic support, and selectively eluting the heparin binding protein from each support.

15. A method for recovering a heparin binding protein from a prokaryotic cell culture, wherein said heparin binding protein is VEGF, the method comprising the steps of
(a) isolating said heparin binding protein from the periplasm of said prokaryotic cell culture;
(b) denaturing said isolated heparin binding protein in a first buffered solution comprising a chaotropic agent and a reducing agent;
(c) incubating said denatured heparin binding protein in a second buffered solution comprising a chaotropic agent and a sulfated polyanionic agent, wherein said sulfated polyanionic agent is dextran sulfate or sodium sulfate, for such a time and under such conditions that refolding of the heparin binding protein occurs, wherein there is about a 2- to 5fold increase in refolded heparin binding protein recovered compared to incubating with no sulfated polyanionic agent; and,
(d) sequentially contacting said refolded heparin binding protein with a cation exchange support; a hydrophobic interaction chromatographic support, and an ion exchange chromatographic support, and selectively eluting the heparin binding protein from each support.

16. The method of claim 14 or 15, wherein the dextran sulfate is between about 3,000 daltons and 10,000 daltons.

* * * * *